(12) United States Patent
Brem et al.

(10) Patent No.: US 8,673,859 B2
(45) Date of Patent: Mar. 18, 2014

(54) GM-CSF COSMECEUTICAL COMPOSITIONS AND METHODS OF USE THEREOF

(75) Inventors: Harold Brem, Bronx, NY (US); Marjana Tomic, Hillsdale, NJ (US)

(73) Assignee: New York University, New York, NY (US)

(*) Notice: Subject to any disclaimer, the term of this patent is extended or adjusted under 35 U.S.C. 154(b) by 578 days.

(21) Appl. No.: 12/052,670

(22) Filed: Mar. 20, 2008

(65) Prior Publication Data
US 2009/0191156 A1  Jul. 30, 2009

Related U.S. Application Data

(60) Provisional application No. 60/895,911, filed on Mar. 20, 2007.

(51) Int. Cl.
A61K 38/00 (2006.01)
A61K 48/00 (2006.01)
A61P 17/00 (2006.01)

(52) U.S. Cl.
USPC ............ 514/18.8; 514/1.1; 514/7.6; 514/9.4; 514/9.7; 514/18.6; 514/44 R

(58) Field of Classification Search
None
See application file for complete search history.

(56) References Cited

U.S. PATENT DOCUMENTS

| | | | |
|---|---|---|---|
| 4,051,842 A | 10/1977 | Hazel et al. | |
| 4,140,122 A | 2/1979 | Kuhl et al. | |
| 4,383,529 A | 5/1983 | Webster | |
| 4,405,712 A | 9/1983 | Vander Woude | |
| 4,603,112 A | 7/1986 | Paoletti et al. | |
| 4,603,146 A | 7/1986 | Kligman | |
| 4,615,697 A | 10/1986 | Robinson | |
| 4,762,915 A | 8/1988 | Kung et al. | |
| 4,769,330 A | 9/1988 | Paoletti et al. | |
| 4,777,127 A | 10/1988 | Suni et al. | |
| 4,861,719 A | 8/1989 | Miller | |
| 4,877,805 A | 10/1989 | Kligman | |
| 4,980,289 A | 12/1990 | Temin et al. | |
| 5,091,309 A | 2/1992 | Schlesinger et al. | |
| 5,194,596 A | 3/1993 | Tischer et al. | |
| 5,217,879 A | 6/1993 | Huang et al. | |
| 5,219,740 A | 6/1993 | Miller et al. | |
| 5,538,739 A | 7/1996 | Bodmer et al. | |
| 5,580,859 A | 12/1996 | Felgner et al. | |
| 5,595,760 A | 1/1997 | Cherif-Cheikh | |
| 5,618,544 A | 4/1997 | Brown | |
| 5,639,480 A | 6/1997 | Bodmer et al. | |
| 5,641,670 A | 6/1997 | Treco et al. | |
| 5,688,530 A | 11/1997 | Bodmer et al. | |
| 5,876,761 A | 3/1999 | Bodmer et al. | |
| 6,190,691 B1* | 2/2001 | Mak ............................ | 424/449 |
| 6,337,318 B1 | 1/2002 | Trigg et al. | |
| 6,372,494 B1 | 4/2002 | Naughton et al. | |
| 6,375,963 B1 | 4/2002 | Repka et al. | |
| 6,528,093 B1 | 3/2003 | Kamei et al. | |
| 6,534,094 B2 | 3/2003 | Moyano et al. | |
| 6,589,540 B1 | 7/2003 | Jo | |
| 6,689,351 B1* | 2/2004 | Pierce et al. ................. | 424/85.1 |
| 6,777,386 B2 | 8/2004 | Trigg et al. | |
| 6,821,524 B2 | 11/2004 | Marini | |
| 7,098,189 B2 | 8/2006 | Malik | |
| 7,109,166 B1 | 9/2006 | Moreau | |
| 2002/0071873 A1* | 6/2002 | Brewitt ......................... | 424/600 |
| 2003/0068297 A1 | 4/2003 | Jain | |
| 2003/0215412 A1 | 11/2003 | Waugh et al. | |
| 2003/0235580 A1 | 12/2003 | Zhang | |
| 2004/0091995 A1 | 5/2004 | Schlom et al. | |
| 2004/0191278 A1 | 9/2004 | Christensen | |
| 2004/0265268 A1 | 12/2004 | Jain | |
| 2007/0224150 A1 | 9/2007 | Chung | |
| 2008/0234194 A1 | 9/2008 | Brem et al. | |
| 2012/0171266 A1* | 7/2012 | Cantwell et al. .............. | 424/401 |

FOREIGN PATENT DOCUMENTS

| | | |
|---|---|---|
| EP | 0 345 242 | 12/1989 |
| EP | 0 386 882 | 9/1990 |
| EP | 0 415 731 | 3/1991 |
| EP | 0 440 219 | 8/1991 |
| EP | 1 369 107 | 12/2003 |
| GB | 2 200 651 | 8/1988 |

(Continued)

OTHER PUBLICATIONS

Acsadi, et al., "Human dystrophin expression in mdx mice after intramuscular injection of DNA constructs", *Nature*, 352(6338):815-8 (1991).

(Continued)

*Primary Examiner* — Michael Pak
(74) *Attorney, Agent, or Firm* — Pabst Patent Group LLP

(57) ABSTRACT

It has been discovered that granulocyte macrophage colony stimulating factor ("GM-CSF") promotes migration of activated (but not differentiating) keratinocytes to wound sites. It was also discovered that GM-CSF increases the quantity and improves the quality of collagen. This growth factor specifically increases migration of keratinocytes of the "wound" phenotype but does not have significant effects upon differentiated keratinocytes. Examples demonstrate reversal of skin impairment in multiple animal models of diabetic skin imparment when provided in an effective amount over an effective time period. The examples also demonstrate the efficacy of the formulations in cosmetic applications. A preferred formulation is a sustained release formulation that delivers sufficient growth factor to the skin and the underlying tissue thereof to increase the rate of keratinocyte migration, as well as collagen deposition and fibroblast proliferation, in the skin to promote rejuvenation of skin injuries resistant to repair due to underlying disease, such as diabetes, or aging.

20 Claims, 4 Drawing Sheets

(56) References Cited

FOREIGN PATENT DOCUMENTS

| | | |
|---|---|---|
| JP | 2003/081866 | 3/2003 |
| WO | WO 89/01973 | 3/1989 |
| WO | WO 89/02468 | 3/1989 |
| WO | WO 89/05349 | 6/1989 |
| WO | WO 90/02806 | 3/1990 |
| WO | WO 90/07936 | 7/1990 |
| WO | WO 90/11092 | 10/1990 |
| WO | WO 90/13649 | 11/1990 |
| WO | WO 91/02805 | 3/1991 |
| WO | WO 92/05266 | 4/1992 |
| WO | WO 92/10578 | 6/1992 |
| WO | WO 92/14480 | 9/1992 |
| WO | WO 93/06223 | 4/1993 |
| WO | WO 93/07282 | 4/1993 |
| WO | WO 93/07283 | 4/1993 |
| WO | WO 93/10218 | 5/1993 |
| WO | WO 93/11230 | 6/1993 |
| WO | WO 93/25234 | 12/1993 |
| WO | WO 93/25698 | 12/1993 |
| WO | WO 94/04184 | 3/1994 |
| WO | WO 94/21792 | 9/1994 |
| WO | WO 94/03622 | 10/1994 |
| WO | WO 95/07994 | 3/1995 |
| WO | WO 00/54745 | 9/2000 |
| WO | WO 01/74317 | 10/2001 |
| WO | WO 02/098365 | 12/2002 |
| WO | WO 03/039444 | 5/2003 |
| WO | WO 03/061686 | 7/2003 |
| WO | WO 2006/014089 | 2/2006 |

OTHER PUBLICATIONS

Adgighitov, et al., "Characterization of tumors induced in adult *Macaca mulata* monkeys with Carr-Zilber strain of *Rous sarcoma virus*", *Neoplasma*, 27(2):159-64, (1980).

Albino, et al., "Class II histocompatibility antigen expression in human melanocytes transformed by Harvey murine sarcoma virus (Ha-MSV) and Kirsten MSV retroviruses", *J. Exp. Med.*, 164(5):1710-22 (1986).

Banks, et al., "Release of the angiogenic cytokine vascular endothelial growth factor (VEGF) from platelets: significance for VEGF measurements and cancer biology", *Br. J. Cancer*, 77:956-964 (1998).

Barba, et al., "Thymidine kinase-mediated killing of rat brain tumors", *J. Neurosurg.*, 79(5):729-35 (1993).

Barrientos, et al., "Growth factors and cytokines in wound healing", *Wound Rep. & Regeneration*, 16(5):585-601 (2008).

Baumann, "Skin ageing and its treatment", *J Pathol.*, 211(2):241-51 (2007).

Bayer, et al., "On the mode of liposome-cell interactions. Biotin-conjugated lipids as ultrastructural probes.", *Biochim. Biophys. Acta.*, 550(3):464-73 (1979).

Beer, et al., "Reduced expression of PDGF and PDGF receptors during impaired wound healing", *J. Invest. Dermatol.*, 109(2):132-8 (1997).

Berkner, "Development of adenovirus vectors for the expression of heterologous genes", *Biotechniques*, 6(7):616-29 (1988).

Berse, et al., "Vascular permeability factor (vascular endothelial growth factor) gene is expressed differentially in normal tissues, macrophages, and tumors", *Mol. Biol. Cell*, 3(2):211-220 (1992).

Bessman, et al., "Infections in the diabetic patient: the role of immune dysfunction and pathogen virulence factors", *J. Diabetes Complications*, 6(4):258-62 (1992).

Bett, et al., "Packaging capacity and stability of human adenovirus type 5 vectors", *J. Virol.*, 67(10):5911-21 (1993).

Brem, et al., "Primary cultured fibroblasts derived from patients with chronic wounds: a methodology to produce human cell lines and test putative growth factor therapy such as GMCSF", *J. Transl. Med.*, 6:75 (2008).

Brogi, et al., "Indirect angiogenic cytokines upregulate VEGF and bFGF gene expression in vascular smooth muscle cells, whereas hypoxia upregulates VEGF expression only", *Circulation*, 90(2):649-652 (1994).

Brown, et al., "Differential expression and localization of insulin-like growth factors I and II in cutaneous wounds of diabetic and nondiabetic mice", *Am. J. Pathol.*, 151(3):715-24 (1997).

Brown, et al., "PDGF and TGF-alpha act synergistically to improve wound healing in the genetically diabetic mouse", *J. Surg. Res.*, 56(6):562-70 (1994).

Buchschacher, et al., "Human immunodeficiency virus vectors for inducible expression of foreign genes", *J. Virol.*, 66(5):2731-9 (1992).

Chatterjee, et al., "Dual-target inhibition of HIV-1 in vitro by means of an adeno-associated virus antisense vector", *Science*, 258(5087):1485-8 (1992).

Cone and Mulligan, "High-efficiency gene transfer into mammalian cells: generation of helper-free recombinant retrovirus with broad mammalian host range", *Proc. Natl. Acad. Sci. U.S.A.*, 81(20):6349-53 (1984).

Connolly, et al., "Tumor vascular permeability factor stimulates endothelial cell growth and angiogenesis", *J. Clin. Invest.*, 84(5):1470-1478 (1989).

Curiel, et al., "High-efficiency gene transfer mediated by adenovirus coupled to DNA-polylysine complexes", *Hum. Gene Ther.*, 3(2):147-54 (1992).

Darby, et al., "Apoptosis is increased in a model of diabetes-impaired wound healing in genetically diabetic mice", *Int. J. Biochem. Cell. Biol.*, 29(1):191-200 (1997).

Deamer and Bangham, "Large volume liposomes by an ether vaporization method", *Biochim. Biophys. Acta.*, 443(3):629-34 (1976).

Debs, et al, "Regulation of gene expression in vivo by liposome-mediated delivery of a purified transcription factor", *J. Biol. Chem.*, 265(18):10189-92 (1990).

Dvorak, "Vascular permeability factor/vascular endothelial growth factor: a critical cytokine in tumor angiogenesis and a potential target for diagnosis and therapy", *J. Clin. Oncol.*, 20(21):4368-4380 (2002).

Einerhand, et al., "Regulated high-level human beta-globin gene expression in erythroid cells following recombinant adeno-associated virus-mediated gene transfer", *Gene Ther.*, 2(5):336-43 (1995).

Enoch and Strittmatter, "Formation and properties of 1000-A-diameter, single-bilayer phospholipid vesicles", *Proc. Natl. Acad. Sci. U.S.A.*, 76(1):145-9 (1979).

Evans, et al., "An engineered poliovirus chimaera elicits broadly reactive HIV-1 neutralizing antibodies", *Nature*, 339(6223):385-8, 340 (1989).

Feige, et al., "Infection, autoimmunity and autoimmune disease", *EXS*, 77:359-73 (1996).

Felgner, et al., "Lipofection: a highly efficient, lipid-mediated DNA-transfection procedure", *Proc. Natl. Acad. Sci. U.S.A.*, 84(21):7413-7 (1987).

Feng, et al., "Neoplastic reversion accomplished by high efficiency adenoviral-mediated delivery of an anti-ras ribozyme", *Cancer Res.*, 55(10):2024-8 (1995).

Ferrara, "Molecular and biological properties of vascular endothelial growth factor", *J. Mol. Med.*, 77(7):527-543 (1999).

Findeis, et al., "Targeted delivery of DNA for gene therapy via receptors", *Trends Biotechnol.*, 11(5):202-5 (1993).

Fisher-Hoch, et al., "Protection of rhesus monkeys from fatal Lassa fever by vaccination with a recombinant vaccinia virus containing the Lassa virus glycoprotein gene", *Proc. Natl. Acad. Sci. U.S.A.*, 86(1):317-21 (1989).

Fitzpatrick, et al., "Reversal of photodamage with topical growth factors: a pilot study", *J. Cosmetic and Laser Therapy*, 5(1):25-34 (2003).

Flexner, et al., "Attenuation and immunogenicity in primates of vaccinia virus recombinants expressing human interleukin-2", *Vaccine*, 8(1):17-21 (1990).

Flotte, et al., "Expression of the cystic fibrosis transmembrane conductance regulator from a novel adeno-associated virus promoter", *J. Biol. Chem.*, 268(5):3781-90 (1993).

(56) References Cited

OTHER PUBLICATIONS

Flotte, et al., "Stable in vivo expression of the cystic fibrosis transmembrane conductance regulator with an adeno-associated virus vector", Proc. Natl. Acad. Sci. U.S.A., 90(22):10613-7 (1993).
Fraley, et al., "Entrapment of a bacterial plasmid in phospholipid vesicles: potential for gene transfer", Proc. Natl. Acad. Sci. U.S.A., 76(7):3348-52 (1979).
Fraley, et al., "Introduction of liposome-encapsulated SV40 DNA into cells", J. Biol. Chem., 255(21):10431-5 (1980).
Geerlings, et al., "Immune dysfunction in patients with diabetes mellitus (DM)", FEMS Immunol. Med. Microbiol., 26(3-4):259-65 (1999).
Gospodarowicz, et al., "Isolation and characterization of a vascular endothelial cell mitogen produced by pituitary-derived folliculo stellate cells", Proc. Natl. Acad. Sci. U.S.A., 86:7311-7315 (1989).
Gough, et al., "Structure and expression of the mRNA for murine granulocyte-macrophage colony stimulating factor", EMBO J., 4(3):645-53 (1985).
Greenhalgh, et al., "PDGF and FGF stimulate wound healing in the genetically diabetic mouse", Am. J. Pathol., 136(6):1235-46 (1990).
Hamre and Procknow, "A new virus isolated from the human respiratory tract", Proc. Soc. Exp. Biol. Med., 121(1):190-3 (1966).
Hartley and Rowe, "Naturally occurring murine leukemia viruses in wild mice: characterization of a new "amphotropic" class", J. Virol., 19(1):19-25 (1976).
Houck, et al., "The vascular endothelial growth factor family: identification of a fourth molecular species and characterization of alternative splicing of RNA", Mol. Endocrin., 5(12):1806-1814 (1991).
Jiao, et al., "Persistence of plasmid DNA and expression in rat brain cells in vivo", Exp. Neurol., 115(3):400-13 (1992).
Kaplan, et al., "Novel responses of human skin to intradermal recombinant granulocyte/macrophage-colony-stimulating factor: Langerhans cell recruitment, keratinocyte growth, and enhanced wound healing", J. Exp. Med., 175(6):1717-28, 1992.
Kaplitt, et al., "Long-term gene expression and phenotypic correction using adeno-associated virus vectors in the mammalian brain", Nat. Genet., 8(2):148-54 (1994).
Keck, et al., "Vascular permeability factor, an endothelial cell mitogen related to PDGF", Science, 246(4935):1309-1312 (1989).
Kit, "Recombinant-derived modified-live herpesvirus vaccines", Adv. Exp. Med. Biol., 251:219-36 (1989).
Koch, et al., "Molecular analysis of the envelope gene and long terminal repeat of Friend mink cell focus-inducing virus: implications for the functions of these sequences", J. Virol., 49(3):828-40 (1984).
Koch, et al., "Interleukin-8 as a macrophage-derived mediator of angiogenesis", Science, 258(5089):1798-1801 (1992).
Kozarsky and Wilson, "Gene therapy: adenovirus vectors", Curr. Opin. Genet. Dev., 3(3):499-503 (1993).
Kunkel, "Rapid and efficient site-specific mutagenesis without phenotypic selection", Proc. Natl. Acad. Sci. U.S.A., 82(2):488-92 (1985).
Lauer, et al., "Expression and proteolysis of vascular endothelial growth factor is increased in chronic wounds", J. Invest. Derm., 115(1):12-18 (2000).
Laurent, et al., "Cell-free translation products of basement membrane RNA from the EHS tumor", Biochim. Biophys. Acta., 908(3):241-50 (1987).
Leibovich and Ross, "The role of the macrophage in wound repair. A study with hydrocortisone and antimacrophage serum", Am. J. Pathol., 78(1):71-100 (1975).
Lerman, et al, "Cellular dysfunction in the diabetic fibroblast: impairment in migration, vascular endothelial growth factor production, and response to hypoxia", Am. J. Pathol., 162(1):303-312 (2003).
Leung, et al., "Vascular endothelial growth factor is a secreted angiogenic mitogen", Science, 246(4935):1306-1309 (1989).
Livant, et al., "The PHSRN sequence induces extracellular matrix invasion and accelerates wound healing in obese diabetic mice", J. Clin. Invest., 105(11):1537-45 (2000).
Loots, et al., "Differences in cellular infiltrate and extracellular matrix of chronic diabetic and venous ulcers versus acute wounds", J. Invest. Dermatol., 111(5):850-7 (1998).
Losordo, et al., "Gene therapy for myocardial angiogenesis", Am. Heart J., 138(2 Pt 2):S132-41 (1999).
Luo, et al., "Adeno-associated virus 2-mediated gene transfer and functional expression of the human granulocyte-macrophage colony-stimulating factor", Exp. Hematol., 23(12):1261-7 (1995).
Luytjes, et al., "Amplification, expression, and packaging of foreign gene by influenza virus", Cell, 59(6):1107-13 (1989).
Madzak, et al., "Efficient in vivo encapsidation of a shuttle vector into pseudo-simian virus 40 virions using a shuttle virus as helper", J. Gen. Virol., 73 (Pt 6):1533-6 (1992).
Malone, et al., "Cationic liposome-mediated RNA transfection", Proc. Natl. Acad. Sci. U.S.A., 86(16):6077-81 (1989).
Manly, et al., "Harvey sarcoma virus genome contains no extensive sequences unrelated to those of other retroviruses except ras", J. Virol., 62(9):3540-3 (1988).
Mann, et al., "Construction of a retrovirus packaging mutant and its use to produce helper-free defective retrovirus", Cell, 33(1):153-9 (1983).
Matsuda, et al. "Role of nerve growth factor in cutaneous wound healing: accelerating effects in normal and healing-impaired diabetic mice", J. Exp. Med., 187(3):297-306 (1998).
Matsuszewska, et al., "Acidic fibroblast growth factor: evaluation of topical formulations in a diabetic mouse wound healing model", Pharm. Res., 11(1):65-71 (1994).
McColl, et al., "Plasmin activates the lymphangiogenic growth factors VEGF-C and VEGF-D", J. Exp. Med., 198(6):863-868 (2003).
McMichael, et al., "Cytotoxic T-cell immunity to influenza", N. Engl. J. Med., 309(1):13-7 (1983).
Mendelson, et al., "Expression and rescue of a nonselected marker from an integrated AAV vector", Virology, 166(1):154-65 (1988).
Miller, "Retrovirus packaging cells", Hum. Gene Ther., 1(1):5-14 (1990).
Miller, et al., "Recombinant adeno-associated virus (rAAV)-mediated expression of a human gamma-globin gene in human progenitor-derived erythroid cells", Proc. Natl. Acad. Sci. U.S.A., 91(21):10183-7 (1994).
Mitani, et al., "Rescue, propagation, and partial purification of a helper virus-dependent adenovirus vector", Proc. Natl. Acad. Sci. U.S.A., 92(9):3854-8 (1995).
Molnar-Kimber, et al., "Impact of preexisting and induced humoral and cellular immune responses in an adenovirus-based gene therapy phase I clinical trial for localized mesothelioma", Hum Gene Ther., 9(14):2121-33 (1998).
Moss and Flexner, "Vaccinia virus expression vectors", Ann. N.Y. Acad. Sci., 569:86-103 (1989).
Mulligan, "The basic science of gene therapy", Science, 260(5110):926-32 (1993).
Mulligan, et al., "Synthesis of rabbit beta-globin in cultured monkey kidney cells following infection with a SV40 beta-globin recombinant genome", Nature, 277(5692):108-14 (1979).
Nabel, et al., "Direct gene transfer with DNA-liposome complexes in melanoma: expression, biologic activity, and lack of toxicity in humans", Proc. Natl. Acad. Sci. U.S.A., 90(23):11307-11 (1993).
Nabel, et al., "Site-specific gene expression in vivo by direct gene transfer into the arterial wall", Science, 249(4974):1285-8 (1990).
Namiki, et al., "Hypoxia induces vascular endothelial growth factor in cultured human endothelial cells", J. Biol. Chem., 270(52):31189-31195 (1995).
Nathan, "Secretory products of macrophages", J. Clin. Invest., 79(2):319-326 (1987).
Neufeld, et al., "Vascular endothelial growth factor (VEGF) and its receptors", FASEB J., 13(1):9-22 (1999).
Nissen, et al., "Vascular endothelial growth factor mediates angiogenic activity during the proliferative phase of wound healing", Am. J. Path., 152(6):1445-1452 (1998).
Oliff, et al., "Molecular cloning of Friend mink cell focus-inducing virus: identification of mink cell focus-inducing virus-like messages in normal and transformed cells", J. Virol., 48(2):542-6 (1983).

(56) References Cited

OTHER PUBLICATIONS

Orringer, et al., "Tretinoin treatment before carbon-dioxide laser resurfacing: a clinical and biochemical analysis", *J. Am. Acad. Dermatol.*, 51(6):940-6 (2004).
Ostro, et al., "Incorporation of high molecular weight RNA into large artificial lipid vesicles", *Biochem. Biophys. Res. Commun.*, 76(3):836-42 (1977).
Padubidri and Browne, "Effect of vascular endothelial growth factor (VEGF) on survival of random extension of axial pattern skin flaps in the rat", *Ann. Plast. Surg.*, 37(6):604-611 (1996).
Papahadjopoulos, et al., "Cochleate lipid cylinders: formation by fusion of unilamellar lipid vesicles", *Biochim. Biophys. Acta*, 394(3):483-91 (1975).
Park, et al., "The vascular endothelial growth factor (VEGF) isoforms: differential deposition into the subepithelial extracellular matrix and bioactivity of extracellular matrix-bound VEGF", *Mol. Biol. Cell*, 4(12):1317-1326 (1993).
Plant, et al., "Generic liposome reagent for immunoassays", *Anal. Biochem.*, 176(2):420-6 (1989).
Ponnazhagan, et al., "Suppression of human alpha-globin gene expression mediated by the recombinant adeno-associated virus 2-based antisense vectors", *J. Exp. Med.*, 179(2):733-8 (1994).
Ram, et al., "In situ retroviral-mediated gene transfer for the treatment of brain tumors in rats", *Cancer Res.*, 53(1):83-8 (1993).
Rivnay, et al., "Use of avidin-biotin technology for liposome targeting", *Methods Enzymol.*, 149:119-23 (1987).
Rosenfeld, et al., "Adenovirus-mediated transfer of a recombinant alpha 1-antitrypsin gene to the lung epithelium in vivo", *Science*, 252(5004):431-4 (1991).
Ru, et al., "Graffi murine leukemia virus: molecular cloning and characterization of the myeloid leukemia-inducing agent", *J. Virol.*, 67(8):4722-31 (1993).
Sabin and Boulger, "*History of Sabin attenuated poliovirus oral live vaccine strains*", J. Biol. Standardization, 1:115-118 (1973).
Samulski, et al., "Helper-free stocks of recombinant adeno-associated viruses: normal integration does not require viral gene expression", *J. Virol.*, 63(9):3822-8 (1989).
Sauter, et al., "Adenovirus-mediated gene transfer of endostatin in vivo results in high level of transgene expression and inhibition of tumor growth and metastases", *Proc. Natl. Acad. Sci. U.S.A.*, 97(9):4802-7 (2000).
Schaefer-Ridder, et al., "Liposomes as gene carriers: efficient transformation of mouse L cells by thymidine kinase gene", *Science*, 215(4529):166-8 (1982).
Senger, et al., "Purification and NH2-terminal amino acid sequence of guinea pig tumor-secreted vascular permeability factor", *Cancer Res.*, 50(6):1774-1778 (1990).
Sorg, et al., "Proposed mechanisms of action for retinoid derivatives in the treatment of skin aging", *J. Cosmet. Dermatol.*, 4(4):237-44 (2005).
Stavri, et al., "Basic fibroblast growth factor upregulates the expression of vascular endothelial growth factor in vascular smooth muscle cells. Synergistic interaction with hypoxia", *Circulation*, 92(1):11-14 (1995).
Stojadinovic, et al., "GMCSF stimulates migration of activated keratinocytes and fibroblasts from patients with chronic wounds", *Wound Rep. & Regeneration*, 15(2):A28 (2007) (Abstract).
Stojadinovic, et al., "A novel, non-angiogenic mechanism of VEGF: stimulation of keratinocyte and fibroblast migration", *Wound Rep. & Regeneration*, 15(2):A68.
Straubinger and Papahadjopoulos, "Liposomes as carriers for intracellular delivery of nucleic acids", *Methods Enzymol.*, 101:512-27 (1983).
Stryer, Biochemistry, pp. 236-240, 1975 (W. H. Freeman, San Francisco, Calif.).
Sun, et al., "A new wound healing agent—sphingosylphosphorylcholine", *J. Invest. Dermatol.*, 106(2):232-7 (1996).
Sun, et al., "Transfection with aFGF cDNA improves wound healing", *J. Invest. Dermatol.*, 108(3):313-8 (1997).

Szoka and Papahadjopoulos, "Fluorescence studies on the mechanism of liposome-cell interactions in vitro", *Biochim. Biophys. Acta.*, 600(1):1-18 (1980).
Szoka, et al., "Procedure for preparation of liposomes with large internal aqueous space and high capture by reverse-phase evaporation", *Proc. Natl. Acad. Sci. U.S.A.*, 75(9):4194-8 (1978).
Takamiya, et al., "Gene therapy of malignant brain tumors: a rat glioma line bearing the herpes simplex virus type 1-thymidine kinase gene and wild type retrovirus kills other tumor cells", *J. Neurosci. Res.*, 33(3):493-503 (1992).
Tsuboi and Rifkin, "Recombinant basic fibroblast growth factor stimulates wound healing in healing-impaired db/db mice", *J. Exp. Med.*, 172(1):245-51 (1990).
Uchida, et al., "Glomerular endothelial cells in culture express and secrete vascular endothelial growth factor", *Am. J. Physiol.*, 260 (1 pt 2):F81-F88 (1994).
Vile and Hart, "In vitro and in vivo targeting of gene expression to melanoma cells", *Cancer Res.*, 53(5):962-7 (1993).
Vile and Hart, "Use of tissue-specific expression of the herpes simplex virus thymidine kinase gene to inhibit growth of established murine melanomas following direct intratumoral injection of DNA", *Cancer Res.*, 53(17):3860-4 (1993).
Wagner, et al., "Transferrin-polycation conjugates as carriers for DNA uptake into cells", *Proc. Natl. Acad. Sci. U.S.A.*, 87(9):3410-4 (1990).
Walsh, et al., "Phenotypic correction of Fanconi anemia in human hematopoietic cells with a recombinant adeno-associated virus vector", *J. Clin. Invest.*, 94(4):1440-8 (1994).
Walsh, et al., "Regulated high level expression of a human gamma-globin gene introduced into erythroid cells by an adeno-associated virus vector", *Proc. Natl. Acad. Sci. U.S.A.*, 89(15):7257-61 (1992).
Wang and Huang, "pH-sensitive immunoliposomes mediate target-cell-specific delivery and controlled expression of a foreign gene in mouse", *Proc. Natl. Acad. Sci. U.S.A.*, 84(22):7851-5 (1987).
Werner, et al., "Induction of keratinocyte growth factor expression is reduced and delayed during wound healing in the genetically diabetic mouse", *J. Invest. Dermatol.*, 103(4):469-73 (1994).
Wetzler, et al., "Large and sustained induction of chemokines during impaired wound healing in the genetically diabetic mouse: prolonged persistence of neutrophils and macrophages during the late phase of repair", *J. Invest. Dermatology* 115: 245-253 (2000).
Williams, et al., "Introduction of foreign genes into tissues of living mice by DNA-coated microprojectiles", *Proc. Natl. Acad. Sci. U.S. A.*, 88(7):2726-30 (1991).
Wilson, et al., "The introduction of poliovirus RNA into cells via lipid vesicles (liposomes)", *Cell*, 17(1):77-84 (1979).
Wolff, et al., "Direct gene transfer into mouse muscle in vivo", *Science*, 247(4949 Pt 1):1465-8 (1990).
Wong, et al., "Fibrin-based biomaterials to deliver human growth factors", *Thromb. Haemost.*, 89(3):573-82 (2003).
Wu and Wu, "Receptor-mediated gene delivery and expression in vivo", *J. Biol. Chem.*, 263(29):14621-4 (1988).
Wu, et al., "Receptor-mediated gene delivery in vivo. Partial correction of genetic analbuminemia in Nagase rats.", *J. Biol. Chem.*, 266(22):14338-42 (1991).
Wu, et al., "Targeting genes: delivery and persistent expression of a foreign gene driven by mammalian regulatory elements in vivo", *J. Biol. Chem.*, 264(29):16985-7 (1989).
Wu, et al., "Incorporation of adenovirus into a ligand-based DNA carrier system results in retention of original receptor specificity and enhances targeted gene expression", *J. Biol. Chem.*, 269(15):11542-0 (1994).
Yamamota, et al., "Effect of topical application of a stable prostacyclin analogue, SM-10902 on wound healing in diabetic mice", *Eur. J. Pharmacol*, 302(1-3):53-60 (1996).
Yang, et al., "MHC class I-restricted cytotoxic T lymphocytes to viral antigens destroy hepatocytes in mice infected with E1-deleted recombinant adenoviruses", *Immunity*, 1(5):433-42 (1994).

(56) References Cited

OTHER PUBLICATIONS

Yantchev, "Studies of the leukemic cell associated antigen(s) in mice with myeloid leukemia (Graffi), using the immunoperoxidase techniques", *Neoplasma*, 26(4):397-404 (1979).

Yap, et al., "Transfer of specific cytotoxic T lymphocytes protects mice inoculated with influenza virus", *Nature*, 273(5659):238-9 (1978).

Yoshida, et al., "Differential endothelial migration and proliferation to basic fibroblast growth factor and vascular endothelial growth factor", *Growth Factors*, 13(1-2):57-64 (1996).

Zenke, et al., "Receptor-mediated endocytosis of transferrin-polycation conjugates: an efficient way to introduce DNA into hematopoietic cells", *Proc. Natl. Acad. Sci. U.S.A.*, 87(10):3655-9 (1990).

Zhou, et al., "Adeno-associated virus 2-mediated transduction and erythroid cell-specific expression of a human beta-globin gene", *Gene Therapy*, 3.223-229 (1996).

Zykova, et al., "Altered cytokine and nitric oxide secretion in vitro by macrophages from diabetic type II-like db/db mice", *Diabetes*, 49:1451-1458 (2000).

* cited by examiner

GM-CSF COSMECEUTICAL COMPOSITIONS AND METHODS OF USE THEREOF

PRIORITY CLAIM

This application claims priority under 35 U.S.C. 119 to U.S. Ser. No. 60/895,911 "GM-CSF Wound Treatment Compositions and Methods of Use Thereof" filed Mar. 20, 2007 by Harold Brem.

STATEMENT REGARDING FEDERALLY SPONSORED RESEARCH OR DEVELOPMENT

This invention was made with government support awarded by the National institutes of Health under Grant Number DK059424. The United States government has certain rights in this invention.

FIELD OF THE INVENTION

The present invention is generally in the field of cosmetic compositions containing granulocyte macrophage colony stimulating factor (GM-CSF) and a method of enhancing repair or regeneration of skin by stimulation of migration of keratinocytes and fibroblasts by administration of the cosmetic GM-CSF composition to the skin for a period of time effective to repair or regenerate skin.

BACKGROUND OF THE INVENTION

Skin, which is the biggest organ of the human body, is composed of epidermis, dermis and subcutaneous fat. It performs various functions such as protection, barrier, temperature controlling, excretion and respiration. With the passage of time, however, those functions rapidly decline and a variety of changes occur to the skin. Physiological changes of the skin with aging, for example, include the decrease in thickness of epidermis, dermis and subcutaneous tissue; the dryness of skin resulting from the moisture reduction according to the changes of lipid composition and content in lipid barrier; and the occurrence of age spots, freckles, pigmentation or various skin lesions. Skin aging is a complex biological process affecting various layers of the skin, but whose major effects are seen in the dermis. There are two biologically independent aging processes that occur simultaneously. The first is intrinsic aging, which affects skin as well as, most likely, the internal organs. The second is extrinsic aging or photo-aging which is the result of exposure to the elements, primarily ultraviolet irradiation. The active oxygen species and free radicals, which can be generated by excess UV rays, air pollution, or fatigue or stress in modern life, oxidize or denature the bio-materials such as proteins, nucleic acids and membrane lipids, aging of the skin. The consequences of innate aging can be observed all over the skin, including areas protected from the sun. In the areas exposed to the sun, particularly the face and the backs of the hands, photoaging damage is superimposed with tissue degeneration due to innate aging. Thus, the most noticeable changes on facial and neck skin, the primary areas that patients are concerned about, result from the combination of intrinsic and extrinsic aging processes. It has been suggested that as much as 80% of facial aging may be ascribed to exposure to the sun, although other factors (i.e. cigarette smoking) can contribute to premature wrinkling. From a biochemical standpoint, photoaging is thought though to be induced mainly by: proteases, mainly metalloproteases, which are overproduced and overrealized by keratinocytes and fibroblasts as a consequence of the interaction with ultraviolet radiation (these proteases are degradative enzymes irreversibly damaging collagen, elastin and hyaluronic acid, eliciting dermis scarring and visible wrinkles); and by oxidative stress, able to eliminate the normal skin antioxidant defenses in a very short time.

Treatments designed to prolong or promote youthful appearance include topical applications of cosmetic preparations, lotions and moisturizer, electrical stimulation, collagen injections and cosmetic surgery.

A variety of cosmetic compositions have been developed to alleviate aging of the skin and some visible results have been obtained in improving skin wrinkles. Various clinical studies have reported on the effects of cosmetic compositions containing retinoids in improving wrinkles, freckles and deposited pigments, especially of the compositions containing retinol (vitamin A) in improving wrinkles, sagging and the reduction in elasticity of skin formed by sunlight. U.S. Pat. Nos. 4,603,146 and 4,877,805 disclose methods for improving skin wrinkles by using retinol that is effective in the synthesis of collagen and the inhibition from the decomposition thereof. However, since retinol may cause skin irritation even with small doses, the use of retinol as an ingredient in cosmetics has been severely limited.

Other studies have demonstrated effectiveness of a combination of retinol and epidermal growth factor (U.S. Pat. No. 6,589,540), or other protein growth factors, alone or in combination (U.S. Pat. Nos. 5,618,544, 6,821,524, U.S. Publication Nos. 2007/0224150, 2004/0265268) or hydroxyl acid compounds (U.S. Pat. No. 7,098,189). Many of the products described in the prior art are not delivered in a sustained release manner, and further do not work by a combination of epidermal regeneration and new collagen production.

A more fundamental and comprehensive approach is needed in treating aging skin that is based on the science and biology of skin. Skin aging is a natural phenomenon that occurs over time. The primary element responsible for accelerating skin aging is overexposure to the sun's harmful rays causing photo damage. But the more important and complex causes of skin aging are biological and are caused by a slowing of the division rate of skin cells and defective cross-linking of collagen and elastin fibers in the skin. With age, the skin fails to regenerate itself as quickly as it used to, and shows common signs of aging in terms of tone and texture. Also, collagen and elastin fibers in the underlying layers of the skin, which provide the scaffolding for the surface layers, begin to weaken and deteriorate with age, causing the skin to lose elasticity and form sags, fine lines, and wrinkles.

From a biological standpoint, an effective plan for rejuvenating and repairing skin must address the rejuvenation of skin cells at both the epidermal and the dermal layers, protection of the rejuvenated cells and cellular activity, stimulation of the production of skin matrix elements, and the sustainability of the rejuvenated conditions over the long term.

It is therefore an object of the present invention to provide compositions that stimulate skin biologic activity and promote skin repair and/or regeneration.

It is a further object of the invention to provide compositions and methods of use thereof to promote skin repair and regeneration with rapid onset of skin repair and regeneration and a reduced frequency of application.

SUMMARY OF THE INVENTION

In the course of wound healing studies on decreasing amputations in the elderly and those with diabetes, discoveries relevant to skin regeneration and repair, it was discovered that GM-CSF promotes migration of activated (but not differentiating) keratinocytes to wound sites. This growth factor specifically increases migration of keratinocytes of the "wound healing" phenotype i.e. activated keratinocytes but does not have significant effects upon differentiated keratinocytes. This discovery has important consequences in skin repair and regeneration.

Examples using two different animal models of diabetic wounds demonstrate that providing an effective amount of GM-CSF over an effective time period promotes fibroblast proliferation as well as collagen production. The GM-CSF also promotes proper alignment of collagen, stimulates infiltration of macrophages and increases subdermal fat, and therefore should induce a smooth appearance of the epidermis, reverse thinning of the skin leading to wrinkling and sagging, and UV-mediated collagen degradation and therefore can be used in resurfacing of skin.

GM-CSF formulations and methods of use thereof are described. A preferred formulation is a sustained release formulation that delivers sufficient growth factor to the skin and surrounding tissue thereof to increase the rate of keratinocyte and fibroblast migration, as well as collagen deposition, proper collagen alignment, infiltration of macrophages as well as increasing sub-dermal fat. Suitable gene therapy formulations are also described. These are applied topically as a lotion, spray, gel, or injected intradermally or subcutaneously.

DETAILED DESCRIPTION OF THE INVENTION

Definitions

Figure 1A:
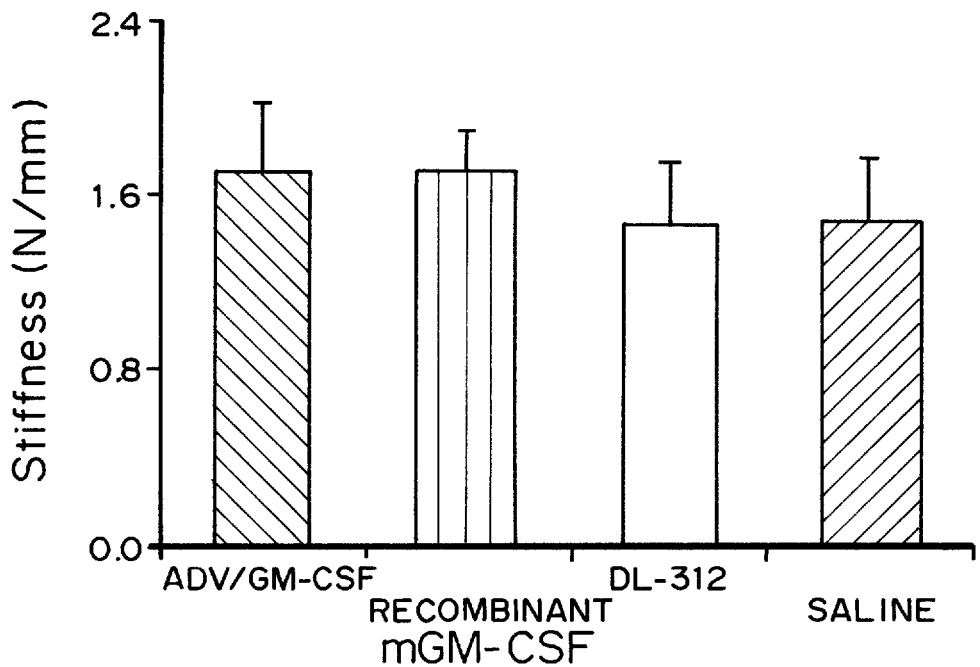
FIGS. 1A-1D are graphs of measured mechanical properties: Stiffness (N/mm) (FIGS. 1A, 1C, respectively) and Load to Failure (A) (FIGS. 1B and 1D, respectively) for NOD Mice at 14 days (FIGS. 1A and 1B) and BKS.Cg-m+/+Lepr$^{db}$ mice at 10 days (FIGS. 1C and 1D), treated as described in the examples.
Figure 1B:
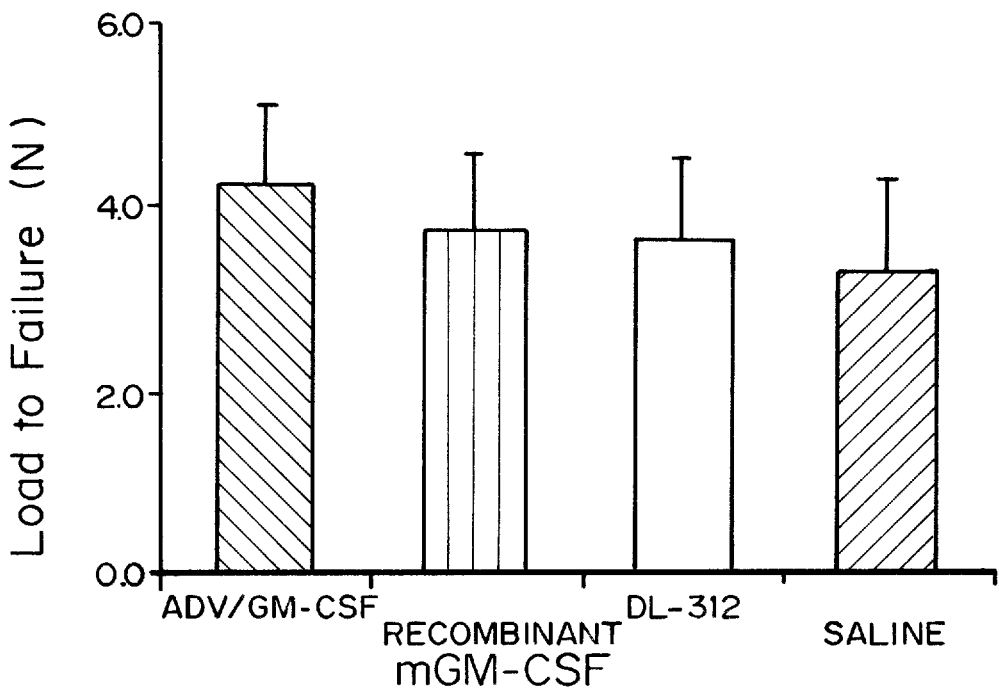
Figure 1C:
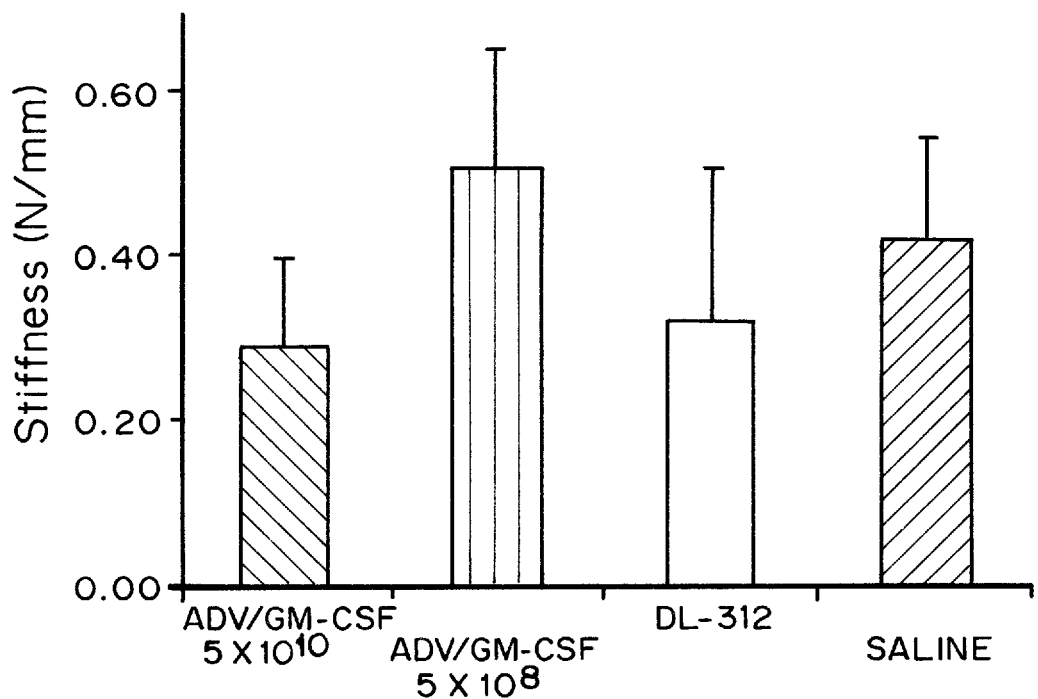
Figure 1D:
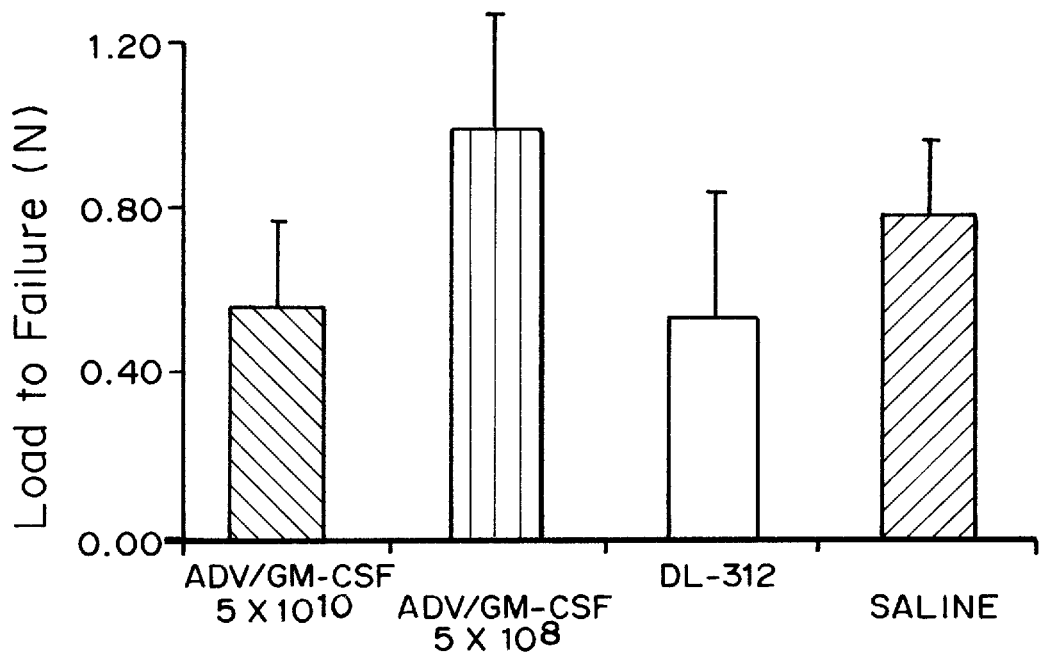
Figure 2A:
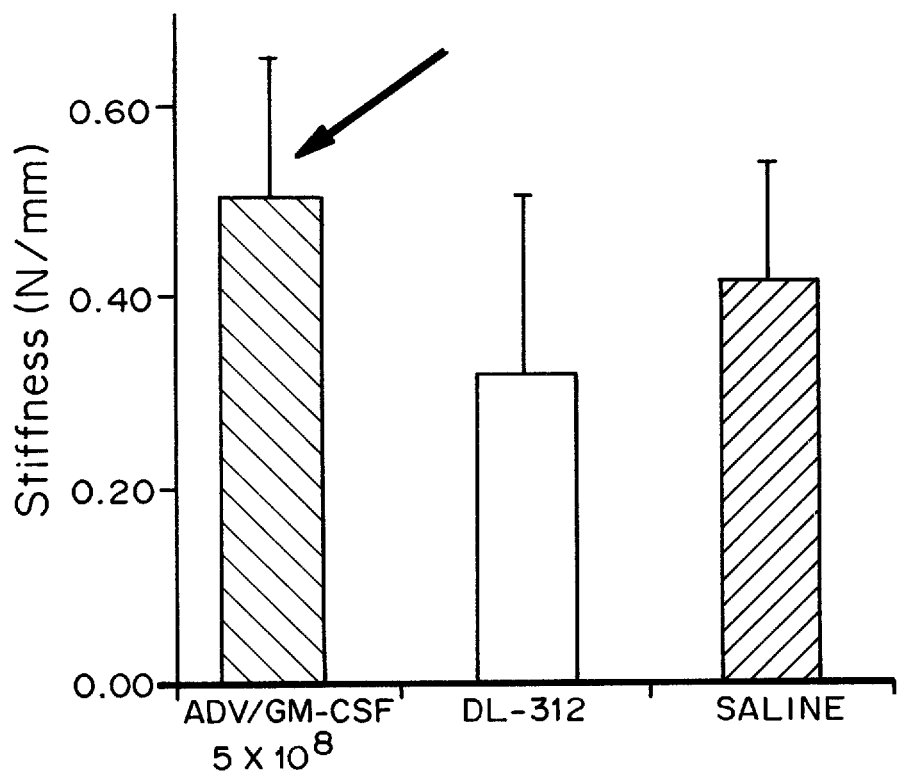
FIGS. 2A and 2B are graphs showing the quantification of measurements of tensile stiffness and breaking strengths (load to failure) of 10 days incisional wounds in Br$^{db}$ (FIG. 2A) and BKS.Cg-m+/+Lepr$^{db}$ (FIG. 2B) db/db mice, treated as described in the examples
Figure 2B:
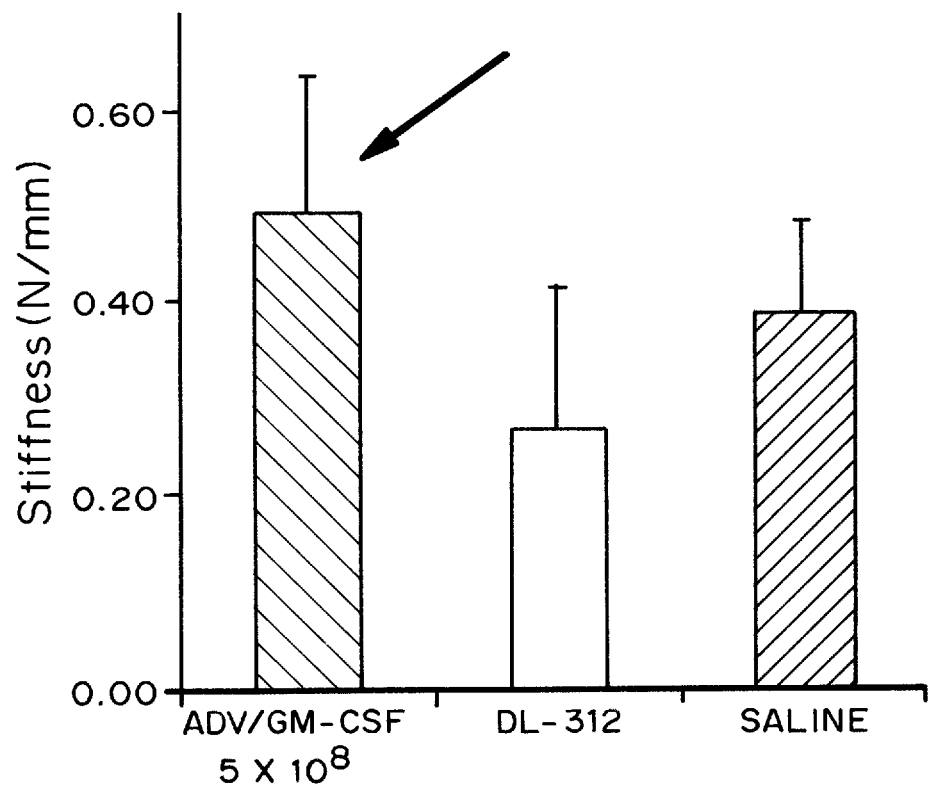

Activated keratinocytes are proliferating cells which have not exited the cell cycle (entered G0). Keratinocytes are "activated" during proliferative responses to injury and hyperproliferative disorders such as psoriasis and hyperplasias. Typically, differentiation or activation will be accompanied by expression of specific markers. The keratins K6 and K16 are two examples of markers expressed by "activated" keratinocytes. Differentiation is also usually marked by polarization of cells to have basal and apical polarity.

I. Formulations

Formulations for local and/or topical administration of GM-CSF for cosmetic applications have been developed. In some embodiments, the GM-CSF is provided in a sustained release formulation, for example, a recombinant expression vector or recombinant virus that provides sustained expression of GM-CSF for prolonged periods of time or which releases an effective amount over time.

A. GM-CSF

As used herein, "GM-CSF" means the gene product of the human GM-CSF gene and naturally occurring variants thereof. GM-CSF is also known as colony stimulating factor 2 (CSF2). Examples of nucleotide and the amino acid sequences of human GM-CSF can be found at the National Center for Biotechnology Information at the ncbi.nlm.nih.gov website. For example, one human GM-CSF polypeptide that may be used in the invention has a sequence with Accession No. NM 000749 (gi: 27437030) (SEQ ID NO: 1, shown below).

```
  1 MWLQSLLLLG TVACSISAPA RSPSPSTQPW EHVNAIQEAR
 41 RLLNLSRDTA AEMNETVEVI SEMFDLQEPT CLQTRLELYK
 81 QGLRGSLTKL KGPLTMMASH YKQHCPPTPE TSCATQIITF
121 ESFKENLKDF LLVIPFDCWE PVQE
```

A nucleotide sequence for the SEQ ID NO: 1 GM-CSF is also available at the ncbi.nlm.nih.gov website. This nucleotide sequence has Accession No. NM 000758 (gi: 27437029) (SEQ ID NO:2, shown below).

```
  1 ACACAGAGAG AAAGGCTAAA GTTCTCTGGA GGATGTGGCT
 41 GCAGAGCCTG CTGCTCTTGG GCACTGTGGC CTGCAGCATC
 81 TCTGCACCCG CCCGCTCGCC CAGCCCCAGC ACGCAGCCCT
121 GGGAGCATGT GAATGCCATC CAGGAGGCCC GGCGTCTCCT
161 GAACCTGAGT AGAGACACTG CTGCTGAGAT GAATGAAACA
201 GTAGAAGTCA TCTCAGAAAT GTTTGACCTC CAGGAGCCGA
241 CCTGCCTACA GACCCGCCTG GAGCTGTACA AGCAGGGCCT
281 GCGGGGCAGC CTCACCAAGC TCAAGGGCCC CTTGACCATG
321 ATGGCCAGCC ACTACAAGCA GCACTGCCCT CCAACCCCGG
361 AAACTTCCTG TGCAACCCAG ATTATCACCT TTGAAAGTTT
401 CAAAGAGAAC CTGAAGGACT TTCTGCTTGT CATCCCCTTT
441 GACTGCTGGG AGCCAGTCCA GGAGTGAGAC CGGCCAGATG
481 AGGCTGGCCA AGCCGGGGAG CTGCTCTCTC ATGAAACAAG
521 AGCTAGAAAC TCAGGATGGT CATCTTGGAG GGACCAAGGG
561 GTGGGCCACA GCCATGGTGG GAGTGGCCTG GACCTGCCCT
601 GGGCCACACT GACCCTGATA CAGGCATGGC AGAAGAATGG
641 GAATATTTTA TACTGACAGA AATCAGTAAT ATTTATATAT
681 TTATATTTTT AAAATATTTA TTTATTTATT TATTTAAGTT
721 CATATTCCAT ATTTATTCAA GATGTTTTAC CGTAATAATT
761 ATTATTAAAA ATATGCTTCT
```

Naturally occurring variants of GM-CSF as well as derivatives of GM-CSF that retain the biological activity of wild-type GM-CSF, i.e. that promote epithelialization of wounds and/or migration of keratinocytes to wound sites, can also be used. Sequences for such variants of GM-CSF are available at the ncbi.nlm.nih.gov website.

As used herein a "derivative" of GM-CSF is a fragment, fusion or modification or analogue thereof, or a fusion or modification of a fragment thereof. A "fragment" of GM-CSF means any portion of the glycoprotein that promotes epithelialization of wounds and/or migration of keratinocytes to wound sites. Typically, the fragment has at least 30% of the activity of full length GM-CSF. It is more preferred if the fragment has at least 50%, preferably at least 70% and more preferably at least 90% of the activity of full length GM-CSF. Most preferably, the fragment has 100% or more of the activity of full length GM-CSF. The derivatives may be made using protein chemistry techniques, for example, using partial proteolysis (either exolytically or endolytically), or by de novo synthesis. Alternatively, the derivatives may be made by recombinant DNA technology.

Modifications of full length GM-CSF, or a fragment thereof, that promote migration of keratinocytes, can also be utilized. Such modifications include deglycosylating the glycoprotein either fully or partially. Other modifications of full length GM-CSF, or a fragment thereof, include amino acid insertions, deletions and substitutions, either conservative or non-conservative, at one or more positions. By "conservative substitutions" is intended to include substitution of an acidic amino acid for another acidic amino (e.g., Asp for Glu and vice versa), substitution of a basic amino acid for another basic acid (e.g., Lys for Arg, and vice versa), substitution of an aliphatic amino acid for another aliphatic acid (e.g., any of Gly, Ala; Val, Ile, Leu can be substituted for other of the Gly, Ala; Val, Ile, Leu amino acids), substitution of an aromatic amino acid for another aromatic amino acid (e.g., substitution of Phe for Tyr and vice versa). Such modifications may be made using the methods of protein engineering and site-directed mutagenesis, as described in Sambrook, et al. 2001 infra. Preferably, the modified GM-CSF or modified GM-CSF fragment retains at least 30% of the activity of full length GM-CSF. It is more preferred if the modified GM-CSF or GM-CSF derivative has at least 50%, preferably at least 70% and more preferably at least 90% of the activity of full length GM-CSF. Most preferably, the modified GM-CSF or modified GM-CSF fragment has 100% or more of the activity of full length GM-CSF.

B. Other Active Agents

Other therapeutic agents, for example, anti-microbial agents, pain relievers, anti-inflammatory agents, vitamins (e.g., vitamin B, C or E), aloe Vera or similar materials, may also be included. These typically enhance moisture retention or act by mechanisms other than through migration of keratinocytes or collagen deposition. GM-CSF can also be administered in combination with skin treatments such as an exfoliant or laser treatment.

C. Carriers

1. Gene Therapy

The principle of gene therapy is that a therapeutic gene must first be efficiently delivered to the specific target cell (Nabel, et al., *Science,* 249:1285-1288 (1990)). Second, it must be expressed and sustained at a certain level to achieve its therapeutic purpose (Sauter, et al., *Proc Natl Acad Sci USA.,* 9:4802-4807 (2002)).

The replication-defective adenovirus vector is a safe and effective vehicle for gene delivery. Adenoviruses (ADV) are ideal gene therapy vectors because they infect a variety of both proliferating and quiescent human cell types, including skin cells, they remain episomal and do not integrate into the human genome. Moreover, they promote stable target gene expression in cells such as keratinocytes, melanocytes and fibroblasts for up to 6 weeks. ADV has been investigated as a gene delivery vector for a variety of therapeutic applications, including cancer, cardiovascular disease and congenital disease. Replication-deficient ADV strains have largely proven to be safe and effective. After a tragic death in a gene replacement trial in which infusion of ADV vector directly into the hepatic artery resulted in fatal systemic inflammation and multi-system failure, subsequent clinical trials in cancer patients established a safe working dose range. Moreover, in recent studies localized ADV administration into sites such as tumors was well tolerated at effective doses without organ toxicity, elevation in serum proinflammatory cytokines or systemic dissemination of vector DNA in animals or people.

Localized GM-CSF gene therapy should increase treatment efficiency and avoid systemic side effects. Safe and effective gene-based delivery of GM-CSF requires efficient targeting to relevant cells, sustained expression at effective levels and localization without systemic absorption. Gene therapy has proven effective in a variety of experimental wound healing models, including on human fetal skin xenografts in SCID mice. ADV-mediated treatment of excisional skin wounds in these mice with platelet-derived growth factor (PDGF) produced an acute inflammatory response but this reaction did not impede wound healing, re-epithelialization, extracellular matrix deposition, granulation or wound closure. Human clinical trials with platelet-derived growth factor (PDGF) are currently underway.

The principle components of gene therapy are a vector or other means of delivering a nucleic acid of interest, and the nucleic acid. Many appropriate viral vectors are known, for example, adenoviral vectors, adeno-associated viral vectors or retroviral vectors. Other means of delivery include liposomes, direct delivery of naked DNA, and hydrogels. The vectors will typically include a promoter that can contain enhancers, inverted terminal repeats (ITRs), inducible promoters, and polyA sequences, followed by a termination sequence. All of these are known to those skilled in the art, and commercially available or described in the literature.

Suitable techniques for cloning, manipulation, modification and expression of nucleic acids, and purification of expressed proteins, are well known in the art and are described, for example, in Sambrook et al (2001) "Molecular Cloning, a Laboratory Manual"#, 3rd edition, Sambrook et al (eds), Cold Spring Harbor Laboratory Press, Cold Spring Harbor, N.Y., USA, incorporated herein by reference.

Growth factor encoding nucleic acids can be placed within linear or circular molecules. They can be placed within autonomously replicating molecules or within molecules without replication sequences. They can be regulated by their own or by other regulatory sequences, as is known in the art. Nucleic acid constructs encoding growth factor may include transcriptional regulatory elements, such as a promoter element, an enhancer or UAS element, and a transcriptional terminator signal, for controlling transcription of the growth factor sequences in the cells. Growth factor encoding nucleic acids can be used in expression cassettes or gene delivery vehicles, for the purpose of delivering a growth factor encoding mRNA, a full-length growth factor protein, a growth factor fusion protein, a growth factor encoding polypeptide, or a fragment of a growth factor encoding polypeptide, into a cell, preferably a eukaryotic cell. A gene delivery vehicle can be, for example, naked plasmid DNA, a viral expression vector, or a growth factor encoding nucleic acid in conjunction with a liposome or a condensing agent.

In one embodiment, the gene delivery vehicle comprises a promoter and a growth factor encoding nucleic acid. Examples of promoters that can be used include tissue-specific promoters and promoters that are activated by cellular proliferation, such as the thymidine kinase and thymidylate synthase promoters. Other preferred promoters include promoters that are activated by infection with a virus, such as the a- and p-interferon promoters, and promoters that can be activated by a hormone, such as estrogen. Other promoters that can be used include the Moloney virus LTR, the CMV promoter, the mouse albumin promoter and adenovirus promoters.

A gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In some embodiments, the gene delivery vehicle is a recombinant retroviral vector. Recombinant retroviruses and various uses thereof have been described in numerous references including, for example, Mann, et al., *Cell,* 33:153-9 (1983), Cane and Mulligan, *Proc. Nat'l. Acad. Sci. USA,* 81:6349 (1984), Miller et al., *Human Gene Therapy,* 1:5-14 (1990), U.S. Pat. Nos. 4,405,712, 4,861,719, and 4,980,289, and PCT Application Nos. WO 89/002,468, WO 89/005,349, and WO 90/002,806. Numerous retroviral gene delivery vehicles can be utilized in the present invention, including for example those described in EP 0,415,731; WO 90/007936; WO 94/003622; WO 93/025698; WO 93/025234; U.S. Pat. No. 5,219,740; WO 93/011230; WO 93/010218; Vile and Hart, *Cancer Res.,* 53:3860-3864, (1993); Vile and Hart, *Cancer Res.,* 53:962-967 (1993); Ram et al., *Cancer Res.,* 53:83-88 (1993); Takamiya et al., *J. Neurosci. Res.,* 33:493-503 (1992); Baba et al., *J. Neurosurg.,* 79:729-735 (1993); (U.S. Pat. No. 4,777,127; GB 2,200,651; EP 0,345, 242 and W091/102805).

Examples of retroviruses that can be utilized include avian leukosis virus (ATCC Nos. VR-535 and VR-247), bovine leukemia virus (VR-13 13, murine leukemia virus (MLV), mink-cell focus-inducing virus (Koch, et al., *J. Vir.,* 49:828 (1984) and Oliff, et al., *J. Vir.,* 48:542-46 (1983)), murine sarcoma virus (ATCC Nos. VR-844,45010 and 45016), reticuloendotheliosis virus (ATCC Nos. VR-994, VR-770 and 4501 I), Rous sarcoma virus, Mason-Pfizer monkey virus, baboon endogenous virus, endogenous feline retrovirus (e.g., RD114), and mouse or rat gL30 sequences used as a retroviral vector. Strains of MLV from which recombinant retroviruses can be generated include 4070A and 15O4A (Hartley and Rowe, *J. Vir.,* 19(1):19-25 (1976), Abelson (ATCC No. VR-999), Friend (ATCC No. VR-245), Graffi (Ru, et al., *J. Vir.,* 67:4722 (1993) and Yantchev, *Neoplasma,* 26:397, (1979)), Gross (ATCC No. VR-590), Kirsten (Albino, et al., *J. Exp. Med.,* 164:1710-22 (1986)), Harvey sarcoma virus (Manly, et al., J. Vir. 62:3540, 1988; and Albino et al., J. Exp. Med. 164: 171 0, 1986) and Rauscher (ATCC No. VR-998), and Moloney MLV (ATCC No. VR-190). A non-mouse retrovirus that can be used is Rous sarcoma virus, for example, Bratislava (Manly, et al., *J. Vir.* 62:3540-43 (1988) and Albino, et al., *J. Exp. Med,* 164:1710-22 (1986)), Bryan high titer (e.g., ATCC Nos. VR-334, VR-657, VR-726, VR-659, and VR-728), Bryan standard (ATCC No. VR-140), Carr-Zilber (Adgighitov, et al., *Neoplasma,* 27:159, 1980), Engelbreth-Holm (Laurent, et al., *Biochem Biophys Acta,* 908:241 (1987), Harris, Prague (e.g., ATCC Nos. VR-772, and 45033), or Schmidt-Ruppin (e.g. ATCC Nos. VR-724, VR-725, VR-354) viruses.

Any of the above retroviruses can be readily utilized in order to assemble or construct retroviral gene delivery vehicles given the disclosure provided herein and standard recombinant techniques (e.g., Sambrook et al., Molecular Cloning: A Laboratory Manual, 2nd Edition (1989), Sambrook et al., Molecular Cloning: A Laboratory Manual, 3'd edition (2001), and Kunkle, *Proc. Natl. Acad. Sci. U.S.A.,* 82:488-92 (1985). Portions of retroviral expression vectors can be derived from different retroviruses. For example, retrovirus LTRs can be derived from a murine sarcoma virus, a tRNA binding site from a Rous sarcoma virus, a packaging signal from a murine leukemia virus, and an origin of second strand synthesis from an avian leukosis vims. These recombinant retroviral vectors can be used to generate transduction competent retroviral vector particles by introducing them into appropriate packaging cell lines.

Recombinant retroviruses can be produced that direct the site-specific integration of the recombinant retroviral genome into specific regions of the host cell DNA. Such site-specific integration is useful for mutating or replacing the endogenous GM-CSF gene. Site-specific integration can be mediated by a chimeric integrase incorporated into the retroviral particle (see Ser. No. 08/445,466 filed May 22, 1995). It is preferable that the recombinant viral gene delivery vehicle is a replication-defective recombinant virus. Packaging cell lines suitable for use with the above-described retroviral gene delivery vehicles can be readily prepared (see WO 92105266) and used to create producer cell lines (also termed vector cell lines or "VCLs") for production of recombinant viral particles. In some embodiments, packaging cell lines are made from human (e.g., HT1080 cells) or mink parent cell lines, thereby allowing production of recombinant retroviral gene delivery vehicles that are capable of surviving inactivation by human serum. The construction of such recombinant retroviral gene delivery vehicles is described in detail in WO 91102805. These recombinant retroviral gene delivery vehicles can be used to generate transduction competent retroviral particles by introducing them into appropriate packaging cell lines. Similarly, adenovirus gene delivery vehicles can also be readily prepared and utilized given the disclosure provided herein (see also Berkner, Biotechniques 6:616-627, 1988, and Rosenfeld, et al., *Science,* 252:43 1-434 (1991), WO 93/07283, WO 93/06223, and WO 93/07282).

A gene delivery vehicle can also be a recombinant adenoviral gene delivery vehicle. Such vehicles can be readily prepared and utilized given the disclosure provided herein and information available in the art (see, e.g., Berkner, Biotechniques, 6:616-29 (1988) and Rosenfeld, et al., *Science,* 252(5004):431-4 (1991), WO 93107283, WO 93106223, and WO 93107282). Adeno-associated viral gene delivery vehicles can also be constructed and used to deliver proteins or nucleic acids to cells in vitro or in vivo. The use of adeno-associated viral gene delivery vehicles in vitro is described in Chatteijee, et al., *Science,* 258:1485-1488 (1992), Walsh, et al., *Proc. Natl. Acad. Sci.,* 89:7257-7261 (1992), Walsh, et al., *J. Clin. Invest.,* 94:1440-1448 (1994), Flotte, et al., *J. Biol. Chem.,* 268:3781-3790 (1993), Ponnazhagan, et al., *J. Exp. Med.,* 179:733-738 (1994), Miller, et al., *Proc. Nat'l Acad. Sci.,* 91:10183-10187 (1994), Einerhand, et al., *Gene Ther.,* 2:336-343 (1995), Luo, et al., *Exp. Hematol.,* 23:1261-1267 (1995), and Zhou, et al., *Gene Therapy,* 3.223-229 (1996). In vivo use of these vehicles is described in Flotte, et al., *Proc. Nat'l Acad. Sci,* 90:1061 3-1061 7 (1993), and Kaplitt, et al., *Nature Genet.,* 8:148-153 (1994).

In another embodiment, a gene delivery vehicle is derived from a togavirus. Such togaviruses include alphaviruses such as those described in WO 95/07994, WO 94/21792, and WO 92/10578. Several different alphavirus gene delivery vehicle systems can be constructed and used to deliver nucleic acids to a cell according to the present invention. Representative examples of such systems include those described in U.S. Pat. Nos. 5,091,309 and 5,217,879.

The recombinant viral vehicle can also be a recombinant alphavirus viral vehicle based on a Sindbis virus. Sindbis constructs, as well as numerous similar constructs, can be readily prepared. Sindbis viral gene delivery vehicles typically comprise a 5' sequence capable of initiating Sindbis virus transcription, a nucleotide sequence encoding Sindbis non-structural proteins, a viral junction region inactivated so as to prevent fragment transcription, and a Sindbis RNA polymerase recognition sequence. Optionally, the viral junction region can be modified so that nucleic acid transcription is reduced, increased, or maintained. As will be appreciated by those of ordinary skill in the art, corresponding regions from other alphaviruses can be used in place of those described above. The viral junction region of an alphavirus-derived gene delivery vehicle can comprise a first viral junction region that has been inactivated in order to prevent transcription of the nucleic acid and a second viral junction region that has been modified such that nucleic acid transcription is reduced. An alphavirus-derived vehicle can also include a 5' promoter capable of initiating synthesis of viral RNA from cDNA and a 3' sequence that controls transcription termination.

Other recombinant togaviral gene delivery vehicles that can be utilized in the present invention include those derived from Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309 and 5,217,879, as well as in WO 92/10578.

Other viral gene delivery vehicles include, for example, those derived from poliovirus (Evans, et al., *Nature,* 339:385 (1989) and Sabin, et al., *J. Biol. Standardization,* 1:1 15 (1973)) (ATCC VR-58); rhinovirus (Arnold, et al., *J. Cell. Biochem., L*401 (1990)) (ATCC VR-1110); pox viruses, such as canary pox virus or vaccinia virus (Fisher-Hoch, et al., *Proc. Natl. Acad. Sci. U.S.A.,* 86:317-21 (1989); Flexner, et al., *Ann. N.Y. Acad. Sci.,* 569:86-103 (1989); Flexner, et al., *Vaccine,* 8:17-21 (1990); U.S. Pat. Nos. 4,603,112 and 4,769,330; WO 89/01 973) (ATCC VR-1 1 1; ATCC VR-2010); SV40 (Mulligan, et al., *Nature,* 277:108-114 (1979)) (ATCC VR-305), (Madzak, et al., *J. Gen. Vir.,* 73: 1533-6 (1992)); influenza virus (Luytjes, et al., *Cell,* 59:1107-113 (1989); McMicheal et al., *The New England Journal of Medicine,* 309: 13-17 (1983); and Yap, et al., *Nature,* 273:238, 1978) (ATCC VR-797); parvovims such as adeno-associated virus (Samulski, et al., *J. Vir.,* 63:3822-8 (1989) and Mendelson, et al., *Virology,* 166:154-65 (1988)) (ATCC VR-645); herpes simplex virus (Kit, et al., *Adv. Exp. Med. Biol.,* 251:219-36 (1989)) (ATCC VR-977; ATCC VR-260); Mulligan, et al., *Nature,* 277:108-114 (1979); human immunodeficiency virus (EPO 3 86,882; Buchschacher, et al., *J. Virol.,* 66:2731-9 (1992); measles virus (EPO 440,219) (ATCC VR-24); A (ATCC VR-67; ATCC VR-1247), Aura (ATCC VR-368), Bebaru virus (ATCC VR-600; ATCC VR-1240), Cabassou (ATCC VR-922), Chikungunya virus (ATCC VR-64; ATCC VR-1241), Fort Morgan (ATCC VR-924), Getah virus (ATCC VR-369; ATCC VR-1243), Kyzylagach (ATCC VR-927), Mayaro (ATCC VR-66), Mucambo virus (ATCC VR-580; ATCC VR-1244), Ndumu (ATCC VR-371), Pixunavirus (ATCC VR-372; ATCC VR-1245), Tonate (ATCC VR-925), Triniti (ATCC VR-469), Una (ATCC VR-374), Whataroa (ATCC VR-926), Y-62-33 (ATCC VR-375), O'Nyong virus, Eastern encephalitis virus (ATCC VR-65; ATCC VR-1242), Western encephalitis virus (ATCC VR-70; ATCC VR-125 1; ATCC VR-622; ATCC VR-1252), and coronavirus (Hamre, et al., *Proc. Soc. Exp. Biol. Med.,* 121:190-3 (1966)) (ATCC VR-740).

Growth factor encoding nucleic acids can be introduced into the skin with agents that can facilitate uptake into cells of the skin using a variety of techniques that are available in the art. For example, a nucleic acid can be combined with a condensing agent to form a gene delivery vehicle. In some embodiments, the condensing agent is a polycation, such as polylysine, polyarginine, polyornithine, protamine, spermine, spermidine, and putrescine. Many suitable methods for making linkages between condensing agents and nucleic acids are known in the art.

Naked DNA is known to be taken up by muscle cells and transiently expressed in vivo, Wolff, et al., *Science,* 247:1465-1468 (1990); and Wolff, *Nature,* 352:815-818 (1991).

Plasmid DNA, which can function episomally, has been used with liposome encapsulation, Capo4 precipitation, and electroporation as an alternative to viral transfections. Clinical trials with liposome encapsulated DNA in treating melanoma illustrates this approach to gene therapy, as reported by Nabel, et al., *Proc. Nat. Acad. Sci. USA.,* 90:11307-11311 (1993) and Jiao, *Experimental Neurology,* 115:400-413 (1992) also reported expression of plasmid DNA. There have been many confirmatory reports since the initial studies.

In some embodiments, a growth factor encoding nucleic acid or polypeptide is associated with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell that has internalized the liposome, thereby releasing its contents into the cytoplasm. Prior to interaction with the surface of a cell, however, the liposome membrane acts as a relatively impermeable barrier that sequesters and protects its contents, for example, from degradative enzymes. Additionally, because a liposome is a synthetic structure, specially designed liposomes can be produced that incorporate desirable features. See, Stryer, Biochemistry, pp. 236-240, 1975 (W. H. Freeman, San Francisco, Calif.); Szoka, et al., *Biochim. Biophys. Acta,* 600:1-18 (1980); Bayer, et al., *Biochim. Biophys. Acta.* 550:464-73 (1979); Rivnay, et al., *Meth. Enzymol.* 149:119-123 (1987); Wang, et al., *Proc. Natl. Acad. Sci. U.S.A.* 84: 7851-5 (1987); Plant, et al., *Anal. Biochem.* 176: 420-6 (1989); and U.S. Pat. No. 4,762,915.

Liposomes can encapsulate a variety of nucleic acid and polypeptide molecules including DNA, RNA, plasmids, expression constructs comprising nucleic acids such those disclosedherein, and GM-CSF polypeptides. Liposomal preparations include cationic (positively charged), anionic (negatively charged) and neutral preparations. Cationic liposomes have been shown to mediate intracellular delivery of plasmid DNA (Felgner, et al., *Proc. Natl. Acad. Sci. USA,* 84:7413-7416 (1987)), mRNA (Malone, et al., *Proc. Natl. Acad. Sci. USA,* 86:6077-6081 (1989)), and purified transcription factors (Debs, et al, *J. Biol. Chem.,* 265:10189-10192 (1990), 1 WO, in functional form. Cationic liposomes are readily available. For example, N[1-2,3-dioleyloxy)propyl]-N,N,N-triethylammonium (DOTMA) liposomes are available under the trademark Lipofectin™, (GIBCO BRL, Grand Island, N.Y.), Transfectace (DDAB/DOPE) and DOTAP/DOPE (Boerhinger). Other cationic liposomes can be prepared from readily available materials using techniques available in the art. See, e.g., Szoka, et al., *Proc. Natl. Acad. Sci. USA,* 75:4194-4198 (1978); and WO 90/11092 for descriptions of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE)e. These materials can also be mixed with the DOTMA and DOTAP starting materials in appropriate ratios. Methods for making liposomes using these materials are well known in the art.

The liposomes can comprise multilamellar vesicles (MLVs), small unilamellar vesicles (SUVs), or large unilamellar vesicles (LUVs). The various liposome-nucleic acid complexes are prepared using methods known in the art. See, e.g., Straubinger, et al., *Methods of Immunology*, 101:512-527 (1983); Szoka, et al., *Proc. Natl. Acad. Sci. USA*, 87:3410-3414 (1990); Papahadjopoulos, et al., *Biochim. Biophys. Acta*, 394:483-91 (1975); Wilson, et al., *Cell*, 17:77-84 (1979); Deamer and Bangham, *Biochim. Biophys. Acta*, 443:629-34 (1976); Ostro, et al., *Biochem. Biophys. Res. Commun.*, 76:836-42 (1977); Fraley, et al., *Proc. Natl. Acad Sci. USA*, 76:3348-52 (1979); Enoch and Strittmatter, *Proc. Natl. Acad Sci. USA*, 76: 145-9 (1979); Fraley, et al., *J. Biol. Chem.*, 255:10431-5 (1980) and Schaefer-Ridder, et al., *Science*, 215:166-8 (1982).

In addition, lipoproteins can be included with a nucleic acid for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of nucleic acids to cells expressing lipoprotein receptors. In some embodiments, if lipoproteins are included with a nucleic acid, no other targeting ligand is included in the composition. Receptor-mediated targeted delivery of GM-CSF nucleic acids to specific tissues can also be used.

Receptor-mediated DNA delivery techniques are described in, for example, Findeis, et al., *Trends in Biotechnol.* 11:202-05 (1993); Chiou, et al. (1994), Gene Therapeutics: Methods and Applications of Direct Gene Transfer (J. A. Wolff, ed.); Wu & Wu, *J. Biol. Chem.* 263:621-24 (1988); Wu, et al., *J. Biol. Chem.*, 269:542-46 (1994); Zenke, et al., *Proc. Natl. Acad. Sci. USA.*, 87:3655-59 (1990); Wu, et al., *J. Biol. Chem.*, 266:338-42 (1991.

In another embodiment, naked nucleic acid molecules are used as gene delivery vehicles, for example, as described in WO 9011 1092 and U.S. Pat. No. 5,580,859. Such gene delivery vehicles can be either DNA or RNA and, in certain embodiments, are linked to killed adenovirus. Curiel, et al., *Hum. Gene. Ther.*, 3:147-154 (1992). Other suitable vehicles include DNA-ligand (Wu, et al., *J. Biol. Chem.* 264:16985-16987 (1989)), lipid-DNA combinations (Feigner, et al., *Proc. Natl. Acad. Sci. USA*, 84:7413 7417 (1989)), liposomes (Wang, et al., *Proc. Natl. Acad Sci. USA.*, 84-7851-7855 (1987)) and microprojectiles (Williams, et al., *Proc. Natl. Acad. Sci. USA.*, 88:2726-2730 (1991)).

One can increase the efficiency of naked nucleic acid uptake into cells by coating the nucleic acids onto biodegradable latex beads. This approach takes advantage of the observation that latex beads, when incubated with cells in culture, are efficiently transported and concentrated in the perinuclear region of the cells. The beads will then be transported into cells when injected into muscle. Nucleic acid-coated latex beads will be efficiently transported into cells after endocytosis is initiated by the latex beads and thus increase gene transfer and expression efficiency. This method can be improved further by treating the beads to increase their hydrophobicity, thereby facilitating the disruption of the endosome and release of nucleic acids into the cytoplasm.

Growth factor-encoding nucleic acids can be introduced into cells using mechanical methods, such as microinjection, liposome-mediated transfection, electroporation, or calcium phosphate precipitation. Alternatively, if it is desired that the cells stably retain the DNA construct, the DNA construct can be supplied on a plasmid and maintained as a separate element or integrated into the genome of the cells, as is known in the art.

Expression of an endogenous growth factor encoding gene in a cell can also be altered by introducing in frame with the endogenous growth factor encoding gene a DNA construct comprising a growth factor targeting sequence, a regulatory sequence, an exon, and an unpaired splice donor site by homologous recombination, such that a homologous recombinant cell comprising the DNA construct is formed. The new transcription unit can be used to turn the growth factor encoding gene on or off as desired. This method of affecting endogenous gene expression is taught in U.S. Pat. No. 5,641,670.

Integration of a delivered growth factor encoding nucleic acid into the genome of a cell line or tissue can be monitored by any means known in the art. For example, Southern blotting of the delivered growth factor encoding nucleic acid can be performed. A change in the size of the fragments of a delivered nucleic acid indicates integration. Replication of a delivered nucleic acid can be monitored inter alia by detecting incorporation of labeled nucleotides combined with hybridization to a growth factor encoding probe. Expression of a growth factor encoding nucleic acid can be monitored by detecting production of growth factor encoding mRNA that hybridizes to growth factor encoding nucleic acid or by detecting growth factor protein. Growth factor protein can be detected immunologically.

In general the viral vectors preferred for gene therapy include human adenoviruses having a 36-kilobase double-stranded DNA genome that undergoes a highly regulated program of gene expression during the normal life cycle of the virus. The advantages of adenoviruses over other chemical, physical, or biological gene transfer techniques include several unique features of this system (Molnar-Kimber, et al., *Hum Gene Ther,* 9(14):2121-33 (1998)). First, adenoviruses infect human skin cells at more than 95% efficiency and do not require that cells are dividing, making a lengthy selection process unnecessary (Kozarsky, et al., *Curr Opin Genet Dev,* 3(3):499-503 (1993); Mulligan, *Science,* 260(5110):926-32 (1993); Kremer, *Gene Ther.,* 2:564-5 (1995); Yang, et al., *Immunity,* 1(5):433-42 (1994); Mitani, et al., *Proc Natl Acad Sci USA,* 92(9):3854-8 (1995)). Second, adenoviruses remain episomal and thus do not normally integrate into the human genome (Bett, et al., *J. Virol.,* 67(10):5911-21 (1993) and Losordo, et al., *Am Heart J.,* 138:132-141 (1999)). Third, adenovirus-mediated gene expression in keratinocytes, melanocytes, and fibroblasts remains stable in vitro for at least 2-6 weeks, depending on the proliferation rate of cells (Feng, et al., *Cancer Res.,* 55(10):2024-8 (1995)). Adenoviral vectors are commonly constructed by deletion of the essential ELAM-1 gene to prevent viral replication.

2. Topical Carriers

The compositions can be administered using a syringe, bandage, transdermal patch, insert, or syringe-like applicator, as a powder/talc or other solid, liquid, spray, aerosol, ointment, foam, cream, gel, paste. This preferably is in the form of a controlled release formulation or sustained release formulation administered topically or injected directly into the skin adjacent to or within the area to be treated (intradermally or subcutaneously). The active compositions can also be delivered via iontophoresis, e.g., as disclosed in U.S. Pat. No. 4,140,122; 4,383,529; or 4,051,842.

The cosmecutical formulations may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents include water and physiologically acceptable buffered saline solutions such as phosphate buffered saline solutions with a substantially neutral pH. Additives may be mixed in with the formulation for maximum or desired efficacy of the delivery system or for the comfort of the patient. Such additives include, for example, lubricants, plasticizing agents, preservatives, gel formers, film formers, cream formers, disintegrating agents, coatings, binders, vehicles, coloring agents, odor controlling agents, humectants, viscosity controlling agents, pH-adjusting agents, and similar agents.

In a preferred embodiment, the compositions contain sufficient amounts of at least one pH buffering agent to ensure that the composition has a final pH of about 3 to about 11, preferably between 6 and 8, most preferably at or near the pH of the skin. Suitable pH modifying agents include, but are not limited to, sodium hydroxide, citric acid, hydrochloric acid, acetic acid, phosphoric acid, succinic acid, sodium hydroxide, potassium hydroxide, ammonium hydroxide, magnesium oxide, calcium carbonate, magnesium carbonate, magnesium aluminum silicates, hydroxyapatite, malic acid, potassium citrate, sodium citrate, sodium phosphate, lactic acid, gluconic acid, tartaric acid, 1,2,3,4-butane tetracarboxylic acid, fumaric acid, diethanolamine, monoethanolamine, sodium carbonate, sodium bicarbonate, triethanolamine, and combinations thereof.

Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

The percent by weight of the active agents present in a formulation will depend on various factors, but generally will be from about 0.01% to about 98% of the total weight of the formulation, and typically about 0.1 to about 90% by weight, more typically less than 50%, most typically in the range of 0.5 to 10%. Reference is also made to the following examples which demonstrate the dose response curves for the formulations applied to appropriate animal models.

Emulsions, Ointments and Creams

The cosmeceutical compositions can be formulated as emulsions for topical application. An emulsion contains one liquid distributed the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

Suitable surfactants include, but are not limited to, anionic surfactants, non-ionic surfactants, cationic surfactants, and amphoteric surfactants. Examples of anionic surfactants include, but are not limited to, ammonium lauryl sulfate, sodium lauryl sulfate, ammonium laureth sulfate, sodium laureth sulfate, alkyl glyceryl ether sulfonate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium and ammonium salts of coconut alkyl triethylene glycol ether sulfate; tallow alkyl triethylene glycol ether sulfate, tallow alkyl hexaoxyethylene sulfate, disodium N-octadecylsulfosuccinnate, disodium lauryl sulfosuccinate, diammonium lauryl sulfosuccinate, tetrasodium N-(1,2-dicarboxyethyl)-N-octadecylsulfosuccinnate, diamyl ester of sodium sulfosuccinic acid, dihexyl ester of sodium sulfosuccinic acid, dioctyl esters of sodium sulfosuccinic acid, docusate sodium, and combinations thereof.

Examples of nonionic surfactants include, but are not limited to, polyoxyethylene fatty acid esters, sorbitan esters, cetyl octanoate, cocamide DEA, cocamide MEA, cocamido propyl dimethyl amine oxide, coconut fatty acid diethanol amide, coconut fatty acid monoethanol amide, diglyceryl diisostearate, diglyceryl monoisostearate, diglyceryl monolaurate, diglyceryl monooleate, ethylene glycol distearate, ethylene glycol monostearate, ethoxylated castor oil, glyceryl monoisostearate, glyceryl monolaurate, glyceryl monomyristate, glyceryl monooleate, glyceryl monostearate, glyceryl tricaprylate/caprate, glyceryl triisostearate, glyceryl trioleate, glycol distearate, glycol monostearate, isooctyl stearate, lauramide DEA, lauric acid diethanol amide, lauric acid monoethanol amide, lauric/myristic acid diethanol amide, lauryl dimethyl amine oxide, lauryl/myristyl amide DEA, lauryl/myristyl dimethyl amine oxide, methyl gluceth, methyl glucose sesquistearate, oleamide DEA, PEG-distearate, polyoxyethylene butyl ether, polyoxyethylene cetyl ether, polyoxyethylene lauryl amine, polyoxyethylene lauryl ester, polyoxyethylene lauryl ether, polyoxyethylene nonylphenyl ether, polyoxyethylene octyl ether, polyoxyethylene octylphenyl ether, polyoxyethylene oleyl amine, polyoxyethelen oleyl cetyl ether, polyoxyethylene oleyl ester, polyoxyethylene oleyl ether, polyoxyethylene stearyl amine, polyoxyethylene stearyl ester, polyoxyethylene stearyl ether, polyoxyethylene tallow amine, polyoxyethylene tridecyl ether, propylene glycol monostearate, sorbitan monolaurate, sorbitan monooleate, sorbitan monopalmitate, sorbitan monostearate, sorbitan sesquioleate, sorbitan trioleate, stearamide DEA, stearic acid diethanol amide, stearic acid monoethanol amide, laureth-4, and combinations thereof.

Examples of amphoteric surfactants include, but are not limited to, sodium N-dodecyl-γ-alanine, sodium N-lauryl-γ-iminodipropionate, myristoamphoacetate, lauryl betaine, lauryl sulfobetaine, sodium 3-dodecyl-aminopropionate, sodium 3-dodecylaminopropane sulfonate, sodium lauroamphoacetate, cocodimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, oleamidopropyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and combinations thereof.

Examples of cationic surfactants include, but are not limited to, behenyl trimethyl ammonium chloride, bis(acyloxyethyl)hydroxyethyl methyl ammonium methosulfate, cetrimonium bromide, cetrimonium chloride, cetyl trimethyl ammonium chloride, cocamido propylamine oxide, distearyl dimethyl ammonium chloride, ditallowedimonium chloride, guar hydroxypropyltrimonium chloride, lauralkonium chloride, lauryl dimethylamine oxide, lauryl dimethylbenzyl ammonium chloride, lauryl polyoxyethylene dimethylamine oxide, lauryl trimethyl ammonium chloride, lautrimonium chloride, methyl-1-oleyl amide ethyl-2-oleyl imidazolinium methyl sulfate, picolin benzyl ammonium chloride, polyquaternium, stearalkonium chloride, sterayl dimethylbenzyl ammonium chloride, stearyl trimethyl ammonium chloride, trimethylglycine, and combinations thereof.

Suitable suspending agents include, but are not limited to, alginic acid, bentonite, carbomer, carboxymethylcellulose and salts thereof, hydroxyethylcellulose, hydroxypropylcellulose, microcrystalline cellulose, colloidal silicon dioxide, dextrin, gelatin, guar gum, xanthan gum, kaolin, magnesium aluminum silicate, maltitol, triglycerides, methylcellulose, polyoxyethylene fatty acid esters, polyvinylpyrrolidone, propylene glycol alginate, sodium alginate, sorbitan fatty acid esters, tragacanth, and combinations thereof.

Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable antioxidants include, but are not limited to, butylated hydroxytoluene, alpha tocopherol, ascorbic acid, fumaric acid, malic acid, butylated hydroxyanisole, propyl gallate, sodium ascorbate, sodium metabisulfite, ascorbyl palmitate, ascorbyl acetate, ascorbyl phosphate, Vitamin A, folic acid, flavons or flavonoids, histidine, glycine, tyrosine, tryptophan, carotenoids, carotenes, alpha-Carotene, beta-Carotene, uric acid, pharmaceutically acceptable salts thereof derivatives thereof, and combinations thereof.

Suitable chelating agents include, but are not limited to, EDTA, disodium edetate, trans-1,2-diaminocyclohexane-N,N,N',N'-tetraaceticacid monohydrate, N,N-bis(2-hydroxyethyl)glycine, 1,3-diamino-2-hydroxypropane-N,N,N',N'-tetraacetic acid, 1,3-diaminopropane-N,N,N',N'-tetraacetic acid, ethylenediamine-N,N'-diacetic acid, ethylenediamine-N,N'-dipropionic acid, ethylenediamine-N,N'-bis(methylenephosphonic acid), N-(2-hydroxyethyl)ethylenediamine-N,N',N'-triacetic acid, ethylenediamine-N,N,N',N'-tetrakis(methylenephosphonic acid), O,O'-bis(2-aminoethyl) ethyleneglycol-N,N,N',N'-tetraacetic acid, N,N-bis(2-hydroxybenzyl)ethylenediamine-N,N-diacetic acid, 1,6-hexamethylenediamine-N,N,N',N'-tetraacetic acid, N-(2-hydroxyethyl)iminodiacetic acid, iminodiacetic acid, 1,2-diaminopropane-N,N,N',N'-tetraacetic acid, nitrilotriacetic acid, nitrilotripropionic acid, nitrilotris(methylenephosphoric acid), 7,19,30-trioxa-1,4,10,13,16,22,27,33-octaazabicyclo[11,11,11]pentatriacontane hexahydrobromide, triethylenetetramine-N,N,N',N'',N''',N'''-hexaacetic acid, and combinations thereof.

Suitable emollients include, but are not limited to, myristyl lactate, isopropyl palmitate, light liquid paraffin, cetearyl alcohol, lanolin, lanolin derivatives, mineral oil, petrolatum, cetyl esters wax, cholesterol, glycerol, glycerol monostearate, isopropyl myristate, lecithin, and combinations thereof thereof.

Suitable humectants include, but are not limited to, glycerin, butylene glycol, propylene glycol, sorbitol, triacetin, and combinations thereof.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays are conveniently delivered from pressurized packs, for example, via a specially shaped closure. Oil-In-Water emulsions can also be utilized in the compositions, patches, bandages and articles. These systems are semi-solid emulsions, micro-emulsions, or foam emulsion systems. Usually such a system has a "creamy white" appearance. Typically, the internal oil phase is in the range in percentage composition of about 10% to about 40% oil by weight and the external phase may contain 80% or more water. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes, These can be made with anionic, cationic, nonionic or amphoteric surfactants, or with combinations especially of the nonionic surfactants.

Inserts

In some embodiments, the active ingredients can be formulated with oleaginous bases or ointments to form a semi-solid composition with a desired shape. For example, the composition can be shaped for easy application to, or insertion into, a wound, ulcer, puncture wound or surgical site. This class of formulations comprises the active ingredients and hydrocarbon-based semisolids. In addition to the active ingredients, these semisolid compositions can contain dissolved and/or suspended bactericidal agents, preservatives and/or a buffer system. The petrolatum component in these bases can be any paraffin ranging in viscosity from mineral oil employing incorporated isobutylene, colloidal silica, or stearate salts to paraffin waxes. White and yellow petrolatums are examples of such systems. Bases of this class can be made by incorporating high-melting waxes into a fluid mineral oil via fusion or by incorporation of polyethylene into mineral oil at elevated temperature. Polysiloxanes (also known as silicones) are suitable for use in these bases and typically have a viscosity in the range of about 0.5 to lo6 centistokes. The organic entities attached to the polysiloxane are preferably lower molecular weight hydrocarbon moieties having from 1 to 8 carbons each, such as lower alkyl, lower alkenyl, phenyl and alkyl substituted phenyl, and phenyl(lower)alkyl, such as benzyl. In such a moiety, each lower alkyl or alkenyl group preferably has 1 to 3 carbons inclusive, such as in a dimethylsiloxane polymer.

Absorption bases can be used with such an oleaginous system. In addition to the active ingredients, additional ingredients with the capacity to emulsify a significant quantity of water are employed. Water-in-oil (w/o) emulsions can be formed wherein the external phase is oleaginous in character. Preservatives/bacteriostats, such as the parabens, buffer systems, etc. can be incorporated into these bases as emulsified aqueous solutions together with the active ingredient. Diverse additives are conveniently used as the emulsifier, and these include, but are not limited to, cholesterol, lanolin (which contains cholesterol and cholesterol esters and other emulsifiers), lanolin derivatives, beeswax, fatty alcohols, wool wax alcohols, low HLB (hydrophobellipophobe balance) emulsifiers, and assorted ionic and nonionic surfactants, singularly or in combination.

Controlled Release Formulations

Controlled or sustained release can be achieved by the addition of time-release additives, such as polymeric structures, matrices, that are available in the art. For example, the compositions may also be administered through the use of hot-melt extrusion articles, such as bioadhesive hot-melt extruded film (see, for example, U.S. Pat. No. 6,375,963). The formulation can comprise a cross-linked polycarboxylic acid polymer formulation, generally described in U.S. Pat. No. 4,615,697. In general, about eighty percent of the monomers of the polymer in such a formulation contain at least one carboxyl functionality. The cross-linking agent should be present at such an amount as to provide enough adhesion to allow the system to remain attached to the target epithelial or endothelial cell surfaces for a sufficient time to allow the desired release to take place.

An insert, transdermal patch, bandage or article can comprise a mixture or coating of polymers that provide release of the active agents at a constant rate over a prolonged period of time. In some embodiments, the article, transdermal patch or insert comprises water-soluble pore forming agents, such as polyethylene glycol (PEG) that can be mixed with water insoluble polymers to increase the durability of the insert and to prolong the release of the active ingredients. Such a water-soluble pore-forming agent can be polyethylene glycol, polypropylene glycol, a mixture or polymer of sugars (lactose, sucrose, dextrose, etc.), salts, poloxamers, hydroxypropylcellulose, polyvinyl alcohol and other water-soluble food grade and other excipients.

The inserts, articles, transdermal patches and bandages may also comprise a water insoluble polymer. Examples of such polymers are ethylcellulose, acrylic resins, co-polymer of methacrylic acid and acrylic acid ethyl ester, polylactic acid, PLGA, polyurethane, polyethylene vinyl acetate copolymer, polystyrene-butadiene copolymer and silicone rubber, or mixtures thereof. For example, polymers sold under trade names Aquacoat ECD 30 and Eudragit RS 30 and NE 30D (registered trademarks of Rhom Tech, Inc.) can be used. These are particularly suitable for administration to sites where pH change can be used to effect release. These rate controlling polymers can be applied using a continuous coating film during the process of spraying and drying with active agents. The rate controlling film prepared with such a polymer is stable during implantation. The film should have enough strength to withstand tear and inner osmotic pressure, and have the stability not to swell or hydrate during the implantation life. In one embodiment, the coating formulation is used to coat pellets comprising the active ingredients that are compressed to form a solid, biodegradable insert.

A polymer formulation can also be utilized to provide controlled or sustained release. Such a polymer formulation can be adjusted to control the release rate of the hyaluronic acid by varying the amount of cross-linking agent in the polymer. Suitable cross-linking agents include divinyl glycol, divinylbenzene, N,N-diallylacrylamide, 3,4-dihydroxy-1,5-hexadiene, 2,5-dimethyl-1,5-hexadiene and similar agents. One example of a polymer for use in such a formulation is Polycarbophil, U.S.P., which is commercially available from B. F. Goodrich Specialty Polymers of Cleveland, Ohio under the trade name NOVEON™-AA1. The United States Pharmacopeia, 1995 edition, United States Pharmacopeial Convention, Inc., Rockville, Md., at pages 1240-41, indicates that polycarbophil is a polyacrylic acid, cross-linked with divinyl glycol.

Other useful bioadhesive polymers that may be used in such a delivery system formulation are mentioned in U.S. Pat. No. 4,615,697. Typically, these polymers would not be used in their salt form, because this would decrease their bioadhesive capability. Such bioadhesive polymers may be prepared by conventional free radical polymerization techniques utilizing initiators such as benzoyl peroxide, azobisisobutyronitrile. Exemplary preparations of useful bioadhesives are provided in U.S. Pat. No. 4,615,697. As will be apparent to those skilled in the art, the composition can be varied to affect certain properties of the formulation. For example, the viscosity can be varied by varying the concentration of therapeutic agents and carriers, or by adding a polymer or gel former.

Alternatively, the growth factor is delivered using a sustained release device. Both non-biodegradable and biodegradable matrices can be used for delivery of genes, although biodegradable matrices are preferred. These may be natural or synthetic polymers, although synthetic polymers are preferred due to the better characterization of degradation and release profiles. The polymer is selected based on the period over which release is desired, generally in the range of at least two to six weeks, although longer periods may be desirable. In some cases linear release may be most useful, although in others a pulse release or "bulk release" may provide more effective results. The polymer may be in the form of a hydrogel (typically absorbing up to about 90% by weight of water), and can optionally be crosslinked with multivalent ions or polymers.

High molecular weight genes can be delivered partially by diffusion but mainly by degradation of the polymeric system. In this case, biodegradable polymers, bioerodible hydrogels, and protein delivery systems are particularly preferred. Examples of non-biodegradable polymers include ethylene vinyl acetate, poly(meth)acrylic acid, polyamides, copolymers and mixtures thereof. Examples of biodegradable polymers include synthetic polymers such as hydroxyacid polymers, for example, polymers of lactic acid and glycolic acid, polyanhydrides, poly(ortho)esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In one embodiment, the polymeric matrix is a microparticle between nanometers and one millimeter in diameter, more preferably between 0.5 and 100 microns for administration via injection. The microparticles can be microspheres, where the gene is dispersed within a solid polymeric matrix, or microcapsules, where the core is of a different material than the polymeric shell, and the gene is dispersed or suspended in the core, which may be liquid or solid in nature. Unless specifically defined herein, microparticles, microspheres, and microcapsules are used interchangeably.

Alternatively, the polymer may be cast as a thin slab or film, ranging from nanometers to four centimeters, a powder produced by grinding or other standard techniques, or even a gel such as a hydrogel. The polymer can also be in the form of a coating or part of a bandage, stent, catheter, vascular graft, or other prosthetic device.

The matrices can be formed by solvent evaporation, spray drying, solvent extraction and other methods known to those skilled in the art.

The release of growth factor from fibrin-based biomaterials was demonstrated by Wong, et al., *Thromb Haemost.*, 89(3):573-82 (2003). Fibrin-based biomaterial preparations can be used as provisional growth matrices for cells important in tissue repair during wound healing in vivo. Growth factor was incorporated into the fibrin biomaterials prior to formation of the Fibrin Sealant clots. Clotting resulted in sustained release of growth factor causing angiogenic activity.

One embodiment provides a sustained-release gel. The gel is made of a pharmaceutical composition including a soluble, gelable peptide salt and up to 30 percent, by weight, of a pharmaceutically acceptable, soluble carrier, and one or more bodily fluids of the patient, wherein the peptide salt automatically forms the gel after interaction with the bodily fluids, and the gel releases the peptide continuously within the patient over a period of at least three days after formation. The pharmaceutical composition that forms the gel can be a solid, or it can further include a solvent, e.g., sterilized water, in an amount less than 50 percent of the amount of solvent required to dissolve the peptide salt and to provide the pharmaceutical composition with a semisolid consistency.

Another embodiment provides a growth factor peptide incorporated in a conventional hydrophobic polymer matrix, e.g. of a polylactide, which is made more accessible for water by introducing a hydrophilic unit, e.g. of polyethyleneglycol, polyvinylalcohol, dextran or polymethacrylamide. The hydrophilic contribution to the amphipathic polymer is given by all the ethylene oxide groups in case of a polyethylene glycol unit, by the free hydroxyl groups in the case of a polyvinylalcohol unit or of a dextran unit, and by the amide groups in the case of a polymethyacrylamide unit.

Many sustained release formulations for delivery of peptides are known. See, for example, U.S. Pat. Nos. 5,595,760; 5,538,739, 5,876,761, 5,639,480, 5,688,530, 6,534,094, 7,109,166, 6,777,386, 6,337,318, and 6,528,093.

Kits and Devices

The formulations may be provided as a packaged cosmeceutical, such as a kit or other container. The kit or container holds an effective amount of GM-CSF for promoting keratinocyte migration, fibroblast proliferation, collagen production, proper collagen alignment, macrophage infiltration in the skin, and increasing subdermal fat and instructions for using the pharmaceutical composition for repairing or regenerating skin. The pharmaceutical composition includes a composition, in an effective amount as defined herein. In some embodiments the composition is provided as part of a bandage. For example, the compositions can be applied to one side of a bandage or a transdermal patch, or the bandage or patch can be saturated with a liquid suspension of the composition.

Liquid compositions can be administered from absorbent materials, such as a bandage, patch or sponge, or as a spray or aerosol (applied to the affected area using a pump-type or aerosol sprayer). The use of a patch or bandage, into which the composition has been incorporated, is advantageous in that it the composition will be slowly and continuously released. Providing the composition in the form of a solution, which may initially be provided in a concentrated liquid form, or as a sterile dissolvable powder, for example, in a packet or syringe, requiring the addition of water, saline or other suitable diluents prior to use may be advantageous.

Solid compositions can be applied by any number of means, including the use of applicators or by patient self-administration. For example, creams, lotions, foams, pastes, ointments, or gels may be administered using an applicator, such as a squeeze-type or plunger-type applicator. Administering the composition as a suppository is advantageous as it provides convenience, ease of application, increased safety and/or neatness. Administering the composition as a cream having low surface tension is advantageous as it provides a uniform wetting action that assists in composition penetration into crypts and crevices of the wound. Such a creamy composition can also act as a moisturizer.

Prolonged controlled release has been achieved using several different devices. Examples include mini-implantable pumps for a variety of drugs especially chemotherapeutics and highly potent neuroactive drugs, silicon tubing with release controlling pores in the ends for birth control agents, and co-axial implants. Currently approved infusion procedures generally use an externally-worn or implanted pump. For example, DUROS™, sufentanil, an osmotic pump designed for 100-day delivery of sufentanil, is currently undergoing clinical testing. This implant is much smaller and easier to administer, and is described in WO 00/54745.

III. Methods of Treatment

A. Local Sustained Release of GM-CSF

The therapeutic agents, including GM-CSF protein or recombinant expression systems that provide sustained release of GM-CSF, may be administered in a single dose, in multiple doses, in a continuous or intermittent manner, depending, for example, upon the recipient's physiological condition. Administration of the compositions may be essentially continuous over an indeterminate period of time, for example, at regular intervals. Alternatively, the compositions can be administered continuously for a pre-selected period of time or in a series of spaced doses.

GM-CSF can be applied in the form of a gene construct that can produce the gene product in vivo. In one embodiment, an adenovirus delivery system is used to deliver GM-CSF in a sustained release fashion in vivo. An adenovirus-GM-CSF (ADV/GM-CSF) expression system has now been tested in diabetic animal models and results indicate that this expression system can be an effective in the repair and regeneration of skin. Other means of obtaining sustained release of an effective amount of compound include providing sustained release formulations such as polymeric delivery systems, mini-pumps, and hydrogels, as described above. These can be loaded with GM-CSF, injected or implanted into the ulcers, where the GM-CSF is released over a therapeutically effective time period.

In one embodiment, GM-CSF is delivered as an injectable and administered in combination with dermabrasion. In this embodiment a single dosing is effective; in other cases, the GM-CSF must be administered two or more times.

In another embodiment, GM-CSF is applied as cream or other topical formulation as described above, preferably providing sustained release over a period of up to two weeks. Administration can be repeated, for example, once a month, as needed.

B. Effective Dosages

In general, for optimal effects, substantially steady rates of GM-CSF are delivered to the site of application. Desirable levels of GM-CSF are those that do not cause adverse side effects. Such an effective dosage can be determined by extrapolation based on animal studies, for example, using a mouse model.

GMCSF stimulates simultaneously four cell types: keratinocytes, fibroblasts macrophages and adipocytes. GM-CSF effects on all these cell types can reverse existing aging effects and prevent new damaging effects. Therefore, the GM-CSF is administered to provide an effective amount to:
1) promote keratinocyte migration, which can induce smooth appearance of epidermis. For example, in dermabrasion (removal or scrubbing off the epidermal layer) or any method of exfoliation it stimulates keratinocytes to cover the damaged areas.
2) Promote fibroblast proliferation, since the more fibroblasts, the more collagen. Thinning of skin is one of the aging signs that lead to wrinkling and sagging. More fibroblasts and more collagen reverses this effect.
3) Promote collagen production by the increased number of fibroblasts. More collagen means thicker dermis, thicker skin protects from UV (prevention) and also reverses existing effects. More collagen means stronger skin, reducing wrinkles and preventing those that are generated by grimacing of the face (such as smiling).
4) Promote proper alignment of collagen that is produced so that it is in an orientation in which it is most stable and less susceptible to degradation.
5) Stimulate infiltration of macrophages. These cells provide number of important factors that can also revive (stimulate) fibroblast and keratinocytes to become more active.
6) GMCSF increases sub-dermal fat, This stimulation of adipocytes may reverse the wrinkles and sagging, because subcutaneous fat is what provides the base for dermis and over the years fat cells get smaller. This leads to more noticeable wrinkles and sagging, as the fat cells cannot "fill in" the damage from the other layers. More subcutaneous fat means "fuller appearance" of skin. This also prevents more wrinkling, because the dermis sits on a solid base that does not give way, it makes it stronger.

The C57BL/KsJ db/db mouse is a particularly useful model since it has been shown to be a clinically relevant model of impaired wound healing. The animals exhibit several characteristics of adult onset diabetes, including obesity, insulin-resistant hyperglycemia and markedly delayed wound closure. C57BL/KsJ-db/db mice, homozygous for the diabetes spontaneous mutation, become identifiably obese around 3 to 4 weeks of age. Elevations of plasma insulin begin at 10 to 14 days and of blood sugar at 4 to 8 weeks. Homozygous mutant mice are polyphagic, polydipsic, and polyuric. The course of the disease is markedly influenced by genetic background. A number of features are observed on the C57BLIKsJ db/db background, including an uncontrolled rise in blood sugar, severe depletion of the insulin-producing beta-cells of the pancreatic islets, and death by 10 months of age. Exogenous insulin fails to control blood glucose levels and gluconeogenic enzyme activity increases. The diabetic mutation is a result of a point mutation in the leptin receptor gene, lepr. This point mutation promotes abnormal splicing creating a stop codon that shortens the intracellular domain of the receptor, so that its signaling capacity is curtailed. The ligand, Leptin, has been shown to be a key weight control hormone that takes a mutant form in the mouse obesity mutation, Lepob (JAX Mice database; http://jaxmice.jax.org/jaxmic-e-cgi/jaxmicedb.cgi).

C57BL/KsJ-db/dbmice exhibit characteristics similar to those of human adult onset diabetes (NIDDM Type 11) as a result of a single autosomal recessive mutation on chromosome 4. Only the homozygous animals develop diabetes. This strain also expresses lower levels of several growth factors and receptors, accounting, at least in part, for the reduced rate of healing (Werner, et al., *J Invest Dermatol*, 103:469-473 (1994)).

The streptozotocin diabetic mouse is another model for studying the pathology of diabetes. Mice are rendered diabetic by intraperitoneal injection of streptozotocin administered for five consecutive days. Streptozotocin-treated mice become hyperglycemic and also show impaired wound healing when compared to healthy animals (Matsuda, et al. *J Exp Med*, 187:297-306 (1998); Brown, et al *Am J Pathol*, 151: 715-724 (1997)). The streptozotocin-induced diabetic mouse has been widely studied and is known to those of skill in the art.

The diabetic mouse model (Geerlings, et al., *FEMS Immunol Med Microbial.*, 3-4:259-265 (1999); Feige, et al., *EXS.*, 77:359-373 (1996); Bessman, *J Diabetes Complications*, 4:258-262 (1992); Loots, et al., *J Invest Dermatol.*, 5:850-857 (1998); Brown, et al., *J Surg Research*, 56:562-570 (1994); Greenhalgh, et al., *Am J Pathol*, 136:1235-1246 (1990); Tsuboi, et al., *J Explorer Med*, 172:245-251 (1990); Matuxzewska, et al., *Pharm Res*, 11:65-71 (1994); Darby, et al, *Int J Biochem Cell Biol*, 29:191-200 (1997); Livant, et al., *J Clin Invest.*, 105:1537-1545 (2000); Yamamota, et al., *Europ J Pharm*, 302:53-60 (1996); Wetzler, et al., *J Invest Dermatol.*, 115:245-253 (2000); Sun, et al., *J Invest Dermatol*, 108:313-318 (1997); Sun, et al., *J Invest Dermatol.*, 106:232-237 (1996); Zykova, et al., *Diabetes*, 49:1461-1458 (2002); Beer, et al., *J Invest Dermatol.*, 109: 132-138 (1997)) has been widely accepted in the study of therapeutic agents that may be effective in the treatment of chronic wounds, it has been successfully used in preclinical testing for other growth factor therapies, and it offers a good model for patients with diabetic foot ulcers.

These animal models were used for assessing optimal levels of CM-CSF to be administered as described below. Those skilled in the art will be able to determine effective dosages for treatment of human patients based on the results described herein and routine dosing studies.

The present invention will be further understood by reference to the following non-limiting examples.

EXAMPLES

These studies were conducted to demonstrate a safe and effective method for gene-based delivery of GM-CSF in an animal model of Type I diabetes, which is characterized by wound repair deficiency. GM-CSF recruits macrophages into fresh wound beds, where they synthesize a variety of growth factors that facilitate wound repair. The studies also demonstrated the hypothesis that localized GM-CSF gene therapy can accelerate acute wound healing in animals with a physiological wound healing impairment. These studies were designed in part to establish the feasibility of safe and effective local GM-CSF gene therapy, and efficacy in the methods described above.

Wound healing is mediated primarily by macrophages. Macrophages constitute a widely dispersed cell population that regulates homeostasis and responds to tissue injury by contributing essential functions during inflammation and repair. After injury, monocytes, the precursors of macrophages, migrate into wounds where they are activated and differentiate into tissue macrophages. By 3-5 days after injury, macrophages are the predominant cell type in the healing tissue. During the inflammation phase, infiltrating neutrophils cleanse the wounded area of foreign particles and bacteria, which are then extruded with the eschar or phagocytosed by macrophages.

The NOD and db/db mice are useful animals models for correlating their delayed wound healing characteristic compared to normal non-diabetic controls. These two strains of mice show diabetic complications similar to human diabetes such as insulin dependency in type I diabetic NOD mice, and obesity in type 2 db/dbmice. Nevertheless, both models display marked delays in healing.

GM-CSF was delivered to freshly induced cutaneous wounds in healing-impaired diabetic mice and the effects on wound healing assessed by quantitative measurement of:
1. time and rate of wound closure, as assessed by digital photography and planimetry
2. wound remodeling, as assessed by histological confirmation of epithelialization, vascularization and collagen matrix deposition
3. tensile strength of the fully healed wound, as measured by biomechanical analysis.

In addition, quantitative cellular and molecular assays were used to provide an initial safety assessment of the specially designed ADV construct. The appearance and persistence of GM-CSF in the wound bed and surrounding tissue was evaluated, and the possible systemic distribution and toxic (especially hepatotoxic) side effects of adenovirus in the test animals.

In order to obtain the maximal amount of information while minimizing the use of animals through experiments of reasonable size and complexity, the following sequence of studies was conducted:
1. Initial dose-finding study to test the hypothesis that locally administered ADV/GM-CSF enhances wound healing in diabetic mice without inducing overt toxicity or uncontrolled inflammation, with a preliminary evaluation of acute and chronic toxicity, using full-thickness excisional wounds.
2. Full characterization of ADV/GM-CSF enhancement of wound healing in diabetic mice by evaluating cellular and molecular indicators of growth factor-induced wound repair, ADV persistence, GM-CSF activity, using full-thickness excisional wounds.
3. Further characterization of ADV/GM-CSF enhancement of wound healing by measuring the biomechanical properties of fully healed incisional wounds to evaluate tensile stiffness and breaking load.

Example 1

Replication-Deficient ADV-GFP-GM-CSF Vector Expresses Both the Green Fluorescent Protein (GFP) Marker and Recombinant Human GM-CSF In Vitro A vector was constructed to deliver recombinant GM-CSF that also contained GFP as a marker protein that could be observed in cells by fluorescence microscopy without further staining.

Materials and Methods for Gene Therapy

The commercially available AdenoVecB system (Invivo-Gen, San Diego, Calif.), a bicistronic vector in which promoters from the human ferritin light and heavy chains (FerL and FerH) have been engineered to direct high-level constitutive expression of two genes, in this case, recombinant GM-CSF and GFP, respectively, in the same cells at comparable levels, was utilized. AdenoVecB is based on replication incompetent linearized (PacI) full-length adenovirus plasmids devoid of the early genes 1 and 3. This double gene expression strategy was used successfully by others for successful intradermal vaccination of mice to increase their T-cell immune response.

cDNA for recombinant human GM-CSF and GFP, was inserted into the AdenoVecB vector and standard calcium phosphate co-precipitation methods were used to transfect the plasmid by into the El-complementing human kidney embryonic cell line, HEK 293. Upon display of cytopathic effect, cells were harvested and the virus was released by three freeze/thaw cycles. The virus was purified on double CsCl gradient and viral particle concentration was measured by absorption at 260 μm. The plaque forming units (pfu) were determined with the standard agarose overlay plaque assay on HEK 293 cells ($2.2\times10^{11}$ pfu/ml). The resulting human GM-CSF vector is referred to as ADV-GFP-hGM-CSF.

ADV-GFP-hGM-CSF and a control vector containing the beta galactosidase (lacZ) reporter gene were transfected separately into subconfluent 293T cells with a multiplicity of infection (moi) of 10 pfu (plaque forming units)/cell. After 24 hr, cells were harvested and GFP activity was visualized by fluorescence microscopy. GFP was expressed in significant numbers of transfected cells containing the GFP vector.

ADV-GFP-GM-CSF vector expresses bioactive GM-CSF in vitro. Peripheral blood monocytes can be induced with GM-CSF and IL-4 to differentiate in vitro into dendritic cells, and this strategy was used to measure bioactivity of recombinant human GM-CSF (rhGM-CSF) in the vector. Human peripheral monocytes were recovered from fresh blood by Ficoll density centrifugation. Monocytes were isolated by two rounds of magnetic activated cell sorting (MACS) through a column of magnetic microbeads labeled with anti-CD 14, which specifically binds to monocytes and macrophages (Miltenyi Biotech, Auburn, Calif.). Monocyte cell purity as assessed by flow cytometry was 80% to 85% after the first MACS round and >95% after the second round.

For the monocyte differentiation assay, CD14+ monocytes were seeded into abTek 8-2311 Permanox chamber slides that had been coated with fibrinogen (1 mg/ml, Calbiochem) and polymerized with thrombin (2.5 U/ml, Sigma) that subsequently was inactivated with medium containing 15% fetal calf serum. Purified CD14+ monocytes were seeded at a concentration of $5\times10^4$/well and treated with recombinant IL-4 (100 ng/ml, Peprotech) and with conditioned virus-inactivated supernatant from ADV-GFP-hGM-CSF infected JC cells that was adjusted to an estimated hGM-CSF concentration of 80 to 100 ng/ml. Control cultures were treated with medium but no growth factors. After 5 days, cells were fixed with 4% paraformaldehyde and incubated for 1 hr at 37° C. with individual dendritie cell-specific antibodies against CD11c, CD83 or CD86, followed by FITC-labeled secondary antibody (minimal cross-reactive Fab' donkey anti-mouse, Jackson Immuno Laboratories). Cells were incubated with 4',6-Diamidino-2-phenylindole (DAPI) to stain the nuclei and observed by fluorescence microscopy. Dendritic cell markers for monocyte differentiation were observed on cells that had been treated with ADV-GFP-hGM-CSF supernatant but not on control cells.

Results

A gene delivery system for bioactive GM-CSF that includes a second independent marker for ADV presence, based on an adenovirus strain that has been engineered for use in human gene therapy, was established. The gene therapy vector chosen is based on the ADV strain DL312 which is a replication-deficient, E1-negative, E3-negative Type 5 adenovirus strain that was developed by Dr. Savio Woo for use in human gene therapy trials. It was modified in collaboration with Dr. Woo to contain either human or murine recombinant GM-CSF. One unique feature of this construct is that it also expresses GFP protein, which is widely used to visualize spatial and temporal patterns of gene expression in vivo and can be used as a quantitative reporter of gene expression levels in individual cells. These studies demonstrated that GFP expression in this construct did not interfere with expression of various target therapeutic genes and that expression levels of GFP and GM-CSF were closely correlated. Therefore one can assess ADV construct presence and expression in cells in and around the wound bed by direct examination with fluorescence microscopy or by immunohistochemical staining with an anti-GFP antibody to localize GFP expression in specific cell types.

Example 2

Measuring Time to Closure in db/db Mice Treated with GM-CSF

Local sustained release of granulocyte macrophage stimulating factor (GM-CSF) using adenovirus vehicle was studied to determine if reversal of the wound healing impairment in type 1 and type 2 diabetic mouse model can be achieved. ADV/GM-CSF was intradermally administered on the dorsum of female BKS.Cg-m+/+Lepr$^{db}$ mice and in non-obese diabetic (NOD) mice using full thickness incisional wound model.

Db/db mice are homozygous for the diabetes spontaneous mutation and as such are a good model of type 2 diabetes. There are three critical aspects of db/db mouse care: 1) monitoring glucose levels; 2) determining the time to onset of diabetes; and 3) providing a pathogen-free environment. In the mouse colony used, pancreatic insulin content decreases significantly at age 12 weeks in females and later in males. Although insulin-dependent diabetes may begin as early as 10 to 12 weeks of age, the time of initial onset peaks at 16 to 20 weeks in females and later in males. Plasma glucose levels are monitored weekly at 12 weeks of age and then bi-weekly starting at 16 weeks. The onset of diabetes is defined as lack of detectable plasma glucose for 2 consecutive weeks. Mild to severe hyperglycemia occurs 3 to 4 weeks after initial diagnosis. Glucose levels are maintained by subcutaneous injections of mixture of intermediate-acting and long-lasting insulin (Novolin 70130). Before each experiment, every animal is evaluated with a portable hemoglobin monitor (DCA2000+ Analyzer, Bayer) to assure that each experimental group has equal and adequate long-term glucose control, as defined by hemoglobin A1e content less than 8.0.

Materials and Methods

Recombinant mouse GM-CSF: (R&D Systems Inc., Minneapolis, Minn., USA) Source A DNA sequence encoding the mature mouse GM-CSF protein sequence (Gough, et al., EMBO J., 4:645-653 (1985)) was expressed in E. coli. The sequence of this mouse GM-CSF is as follows (SEQ ID NO: 3).

```
  1 MWLQNLLFLG IVVYSLSAPT RSPITVTRPW KHVEAIKEAL

41 NLLDDMPVTL NEEVEVVSNE FSFKKLTCVQ TRLKIFEQGL

81 RGNFTKLKGA LNMTASYYQT YCPPTPETDC ETQVTTYADF

121 IDSLKTFLTD IPFECKKPGQ K
```

The 125 amino acid residue recombinant methionyl form of mouse GM-CSF has a predicted molecular mass of approximately 14.8 kDa. Purity: greater than 97%, as determined by SDS-PAGE and visualized by silver stain. Endotoxin Level: less than 0.1 ng per 1 mg of the cytokine as determined by the LAL method. Activity: The biological activity of recombinant mouse GM-CSF was measured by proliferation of the factor-dependent murine cell line, DA-3 (Ihle, et al., 1984, Advances in Viral Oncology, GKlein, ed. Raven Press, New York, N.Y. 4:95-137). The $ED_{50}$ for this effect is typically 0.1-0.3 ng/mL. Formulation: Lyophilized from a 0.2 mm filtered solution in PBS containing 50 mg of bovine serum albumin per 1 mg of cytokine. Reconstitution: It is recommended that sterile phosphate-buffered saline containing at least 0.1% human serum albumin or bovine serum albumin be added to the vial to prepare a stock solution of no less than 5 mg/mL of the cytokine. Storage: Lyophilized samples are stable for greater than six months at −20° C. to −70° C. Upon reconstitution, this cytokine can be stored under sterile conditions at 2'-4° C. for one month or at −20° C. to −70° C. for three months without detectable loss of activity. Avoid repeated freeze-thaw cycles.

All animal procedures were performed with Mount Sinai School of Medicine's Institutional Animal Care and Use Committee. Two strains of diabetic mice were obtained from the Jackson Laboratory (Bar Harbor, Me.): Fifty-seven female BKS.Cg-m+/+Lepr$^{db}$ type 2 diabetic mice (8-week old) were used. Fifty-six Type 1 NOD mice arrived at the facility at 7 weeks old of age, and were reared at the barrier facility until 75% incidence of diabetes was obtained. All animals were housed in a facility with a 2-hr light/dark cycle and temperature maintenance. Water and standard rodent diet were given ad libitum, with the exception during fasting for 12 hours when they were only given water.

Female NOD mice initiate their decrease in pancreatic insulin content at approximately 12 weeks old while diabetes onset in males occurs at a later time. For this reason, females were chosen to demonstrate diabetes characteristic. Although IDDM may initiate as early as 10 to 12 weeks, peak incidence is attained only between 16 to 20 weeks in females, and later in males. Weekly glucose monitoring was performed by measuring plasma glucose levels at 12 weeks of age, then bi-weekly starting at 16 weeks of age. IDDM is usually indicated when plasma glucose levels reach ≥200 mg/dl for 2 consecutive weeks. Mild to severe hyperglycemia occurs in 3-4 weeks from initial diagnosis. Beddings were changed constantly since these adult diabetic mice urinated excessively (polyuria). A mixture of intermediate acting and long lasting insulin (Novolin 70/30, Novo Nordisk) was administered, subcutaneously, to control glucose. Before starting an experiment a portable monitor was used to measure hemoglobin A1c (DCA2000+Analyzer, Bayer) to assure that the groups have equal and good glucose control (hemoglobin A1c<8.0). The animals were wounded at 28 weeks of age and tested 14 days later.

Diabetes in these mice is carefully maintained by measuring HbA1C in each mouse prior to surgery and by subcutaneous injections of a mixture of intermediate-acting and long-lasting insulin (Novolin 70130) to maintain serum glucose levels. Mice are observed daily for signs of distress and any moribund animals sacrificed on humane grounds and subjected to blood HbA1c analysis, gross necropsy and examination of the wound site to determine whether the wound, ADV treatment or underlying diabetes may have produced adverse affects.

The BKS.Cg-m+/+Lepr$^{db}$ mice were divided into 4 groups based on administered treatment: ADV/GM-CSF 5×10$^8$ vp/wound (group I, n=12), ADV/GM-CSF 5×10' vp/wound (group 11, n=13, DL-3 12 vehicle positive control 5×10$^8$ vp/wound (group 111, n=15), and saline, negative control (group IV, n=15). NOD mice were divided into 4 groups based on wound treatment: ADV/GM-CSF 10$^8$ vp/wound (group I, n=14), recombinant GM-CSF 10 µg/wound (group 11, n=14), DL-3 12 5×10$^8$ vp/wound (group 111, n=14), and saline (group IV, n=14).

Wounding.

The NOD mice were acclimatized for 2 weeks by being placed in individual cages prior to wounding. The animals were shaved at least one day prior to wound creation, and then anesthetized with a mixture of ketamine and xylazine during the wounding. Wounding consisted of a 30-min linear incisional wound initiated 5 min below the last cervical vertebra on the dorsum of each animal in a superior-inferior direction, and the incision was closed with six #5 black braided nylon sutures at 5-min intervals.

8 weeks old female BKS.Cg-m+/+Lepr$^{db}$ mice were anesthetized by intraperitoneal (IP) injection of a ketamine and xylazine mixture and shaved the day before experimentation. Full thickness wounds 1.4 cm diameter were made with a template (George Tieman Inc., NY) and the edges were tattooed. The marked area was excised with scissors to remove the epidermis, dermis, and panniculus carnosus. An 0.8 cm full-thickness circle of skin were removed from the middle of the back. Under current standards of wound care, ulcers in diabetic patients take between 56 and 90 days to heal (if indeed they do heal), but full thickness wounds in these diabetic mice heal within 34 days.

The wounds were digitally photographed at a fixed distance from the wound on the day of surgery, every 4 days thereafter and on the day of closure. A ruler was placed in the field of the photograph, labeled with the mouse's identification number and the date. The digital images were measured using Med-Data Systems' Wound Imager Program and the area was calculated by planimetry. Complete healing is defined by 100% epithelialization with no drainage. Serum glucose content was monitored carefully in each mouse by Hemoglobin A1 c measurement (DCA 2000+Analyzer, Bayer Corp).

Treatment Administration:

A volume of 200 µl of treatment was intradermally administered into the third suture site of the wound in the NOD mice.

Full-thickness excisional wounds were produced in glucose-controlled BKS.Cg-m+/+Lepr$^{db}$ mice and treated with injections of ADV-mGM-CSF. ADV constructs or controls were injected intradermally up to a maximum volume of 400 pl at three sites around the wound perimeter, which is marked with indelible ink. The dose range was selected in half-log units to flank 1×10$^8$ PFUs. Treatment groups are illustrated in the tables. The wounds were dressed with a clear occlusive dressing and after recovery, the mice returned to their cages and observed daily to assess wound healing.

Mice were observed daily, and wound healing and adverse effects assessed quantitatively weekly for 3-8 weeks. Enhanced healing is defined as a statistically significant decrease in the time to closure, an increase in the rate of healing as well as an increase in the extent of epithelialization, angiogenesis and collagen deposition in ADV/GMS-CF-treated mice versus mice that are treated with ADV alone or with saline.

Two mice from each treatment group were sacrificed on Days 7, 14 or 21 after surgery and the wound site excised along with a 2 mm margin of non-wounded skin. One-third of each sample was fixed in formalin-free Zinc-Tris buffer fixative for routine histology processing; one-third was used for analysis of GFP protein expression by fluorescence microscopy; and one-third was used for later isolation of DNA and RNA to measure ADV presence and GM-CSF expression. Blood samples were collected by cardiac puncture and separated serum frozen for later analysis of serum enzyme markers of liver and kidney function. Each animal underwent gross necropsy with special attention to the liver to look for adverse effects from ADV treatment, portions of the liver, kidney, spleen and lung.

Mechanical Testing.

Biomechanical testing of skin tensile strength confirmed that the quality of wound healing is compromised in db/db mice. Skin mechanical properties reflect the inherent structural and functional characteristics of the skin and provide additional information about the progression of wound healing that complement measures of contraction and histology. The db/db model was standardized by comparing the characteristics of healed cutaneous wounds in diabetic mice. Briefly, a 30-mm linear incisional wound was created on the backs of 7-week-old anesthetized db/db mice in the superior-inferior direction, and the incisions were closed with six #5 nylon sutures at 5 mm intervals. Sutures were removed after 7 days. Healing was assessed after 7, 14 or 21 days. A single 8 mm×30 mm skin sample was taken perpendicular to the wound (excising the third suture site) with a template, and their breaking strength was measured with a servohydraulic materials test system (Instron, Canton, Mass., USA). The failure load (i.e., maximal force supported) of wounded skin samples in diabetic mice was only 45% of the intact skin strength on day 21. Importantly, these results demonstrate that mechanical testing is sensitive to changes that occur during the progression of wound healing and can be used as a tool to measure the quality of healing.

The BKS.Cg-m+/+Lepr$^{db}$ mice were sacrificed at days 10 and 21 post injury for mechanical properties analyses of the excised skin (healed wounds). Similarly, on postoperative day 14, mechanical testing was performed on excisional wounds obtained from NOD nice. Mechanical properties of linear incisional wounds were assayed using tensiometry. 30 mm×8 mm skin strip perpendicular to the 3rd incision was excised and used for tensiometry assays.

A tensiometer was used to test the samples due to its known high reliability as an assay of wound healing. The measurements taken give an insight into the mechanical properties of the skin. The strip of skin was immediately placed in 1×PBS in ice-water bath to prevent desiccation; followed by mechanical testing. Each skin sample was clamped between sandpaper-covered plates with a consistent grip-to-grip gauge length of 15 mm. Samples were centered relative to the clamps by using a custom-made alignment apparatus. The samples were attached via the clamps to the actuator of an Instron servohydraulic materials testing system (model 8872, Canton, Mass., USA). Tensile loads were measured using a 2.5 lb. (11.1 N) load transducer (Transducer Techniques, Temecula, Calif., USA). A preload of 0.02 N was then maintained for 2 minutes to define the initial length needed for engineering strain computations. For the preloaded skin sample, the grip-to-grip distance (i.e., specimen length) was measured with precision calipers, and the width was similarly measured along the length of the sample. Immediately following preloading, the sample will be loaded to failure at 0.1 mm/sec. Two measurements are taken from each skin sample: tensile stiffness (a measure of the amount of force required to deform the skin, or extensibility) and tensile failure (or breaking load), a measure of the force required to break the sample (see FIGS. 1A-D).

Histology: Embedding Procedure and Stains.

The tissues excised during surgery were fixed for later histochemical analysis and comparison with samples from the healing wounds as "Day 0" controls. Wounds were digitally photographed at a fixed distance from the wound and the wound area from these images measured by planimetry every 4 days for 3 weeks or until the wound is completely closed. Histological evaluation was performed with day 10 wounds of BKS.Cg-m+/+Lepr$^{db}$ mice to correlate wound biomechanical results. Freshly excised wounds, 30 mm×8 mm skin strip perpendicular to the third incision was obtained 10 days post wounding in BKS.Cg-m+/+Lepr$^{db}$ mice and 14 days post wounding in NOD mice. The excised skin were fixed overnight in 4% parafomaldehyde, bisected and processed for paraffin embedding. Five-micron sections were cut and stained with (1) H&E staining, for evaluation of re-epithelialization, (2) Mason trichrome. Immunohistochemistry were performed on sections with MOMA-21anti-CD68 (macrophages). Investigators blinded to the treatment protocol will perform the assessments. Fixation with 4% paraformaldehyde requires specimen transfer into 70% ethanol after 24-hours of fixation. If this is not performed, antigen retrieval is necessary for any immunohistochemistry, or allow fixation in Zinc-Tris instead.

Stained specimens were graded at the incisional site of the healed wound: 1) H&E based on a) epithelialization: 1=complete; 0=incomplete, b) number of cells/high power field (HPF) at ×40 magnification, c) Inflammation: 2=chronic; 1=acute; O=none, 2) Mason Trichrome based on granulation: 1 complete (100%) Collagen: 1=complete (100%), Collagen %/Granulation Tissue % Ratio: Equals 1; Immunohistochemistry by counting the amount of cells per HPF; 3) MOMA-2 or CD-68, number of macrophages/HPF.

Specialized cell analysis included:

a. Detection of granulation tissue using immunostaining procedures and markers specific for granulation (e.g., increased hydroxyproline content, where hydroxyproline content is a measure of collagen formation).

b. Macrophages by immunostaining with m use Mcrophage markers (MOMA) a general macrophage marker, and MOMA-2, which recognizes mature macrophages, monocytes and some precursors.

c. myofibroblasts by immunostaining with alpha smooth muscle actin (aSMA), a marker for maturation of granulation tissue. Myofibroblast cell density is a gross measure of the proliferative phase of wound repair.

d. Endothelial cells by CD31.

e. Angiogenesis by immunostaining for alpha smooth muscle actin (aSMA), a marker for arterioles and myofibroblast cell proliferation, and for mouse PECAM (CD31), a direct marker of both progenitor and differentiated endothelial cells during angiogenesis.

f. Collagen fiber density and arrangement by staining with Mason trichrome and Sirius red.

For immunohistochemical staining, sections were deparaffinized, rinsed in xylene and rehydrated, then depleted of endogenous peroxidase by incubation with 3% H202 and treated with 2% ovalbumin to block non-specific antibody binding. Antibodies were visualized with standard biotin/streptavidin/horseradish peroxidase staining methods with appropriate isotype controls.

Statistical Analysis

All data were analyzed by 1-tailed Student's t test. The results were expressed as mean±SD. The level of statistical significance in comparison between the groups was set at a p value of less than 0.05. Statistical significance is met when treatment with ADV/GM-CSF is compared and resulted to $p=0.05$ as compared to both saline and vehicle controls. Results On postoperative day 21, the stiffness (mean±SD) were 1.49±0.3, 1.13±0.2, and 1.17±0.15 N/mm for groups I, 111, and IV respectively in BKS.Cg-m+/+Lepr$^{db}$ mice ($p=0.03$ and $p=0.02$). Histological analysis with H&E stain revealed increased number of cells in ADV/GM-CSF 5×10$^8$ vp treated wounds versus vehicle and saline treated control wounds ($p=0.042$ and $p=0.005$ 1).

Outcome Measures

Time and rate of healing. The wounds were digitally photographed at a fixed distance from the wound on the day of wounding, then every 4 days for 3 to 8 weeks or until the day of closure, whichever came first. A ruler was placed in the field of the photograph labeled with the animal's identification number and the date. The area of the wound was measured by planimetry using Wound Imager 2.0 by MedSystems. The images and related information was stored in an electronic database for later comparison and analysis. Both time to closure (days) and rate of closure (mm/week) were compared between analogous doses of ADV/GM-CSF and ADV-GFP, and between ADV/GM-CSF and saline control groups with Student's t test.

Wound Remodeling.

Tissues were embedded in paraffin and processed for routine histology and immunohistochemistry to measure the extent of epithelialization, angiogenesis, collagen deposition and infiltration of macrophages, fibroblasts and myofibroblasts. General tissue composition and structure were evaluated on sections stained with hematoxylin and eosin (H&E) staining. Re-epithelialization was measured by semiautomatic computer based morphometric analysis to quantify total cell density, repopulation with macrophages and myofibroblasts, and angiogenesis in each sample. In addition, samples were analyzed for evidence of pathologies such as formation of cavernous capillaries or granulomas (a foreign body reaction) or local necrosis.

GM-CSF Transduction of Keratinocvtes, Fibroblasts, Macrophages and Endothelial Cells in Wound Bed.

The number of ADV-transduced keratinocytes, fibroblasts, macrophages and endothelial cells in and around the wound bed were evaluated through migration patterns established via wound scratch assays.

Exogenous GM-CSF Gene Expression.

Skin samples were stained with a polyclonal goat anti murine GM-CSF antibody (RDS, Inc) to define GM-CSF protein expression in ADV/GM-CSF animals. GM-CSF expression was correlated with the presence of adenovirus particles in these cells by double labeling immunohistochemistry with an antibody to ADV (Access Biomedical). Sections were counterstained with hematoxylin and/or hematoxylin and eosin (H&E) to identify the cell types. In a second approach, reserved tissues were homogenized and subjected to RT-PCR analysis with sets of primers that are designed to distinguish exogenous recombinant GM-CSF in the vector construct from endogenous native GM-CSF sequence. This analysis confirms recombinant GM-CSF expression and permit correlation of GM-CSF expression levels with transduction of keratinocvtes, fibroblasts, macrophages and endothelial cells in wound bed.

ADV Distribution and Persistence.

There are two important reasons to determine whether subcutaneous injection of ADV/GM-CSF results in systemic dissemination of the vector. 1) ADV readily infects a variety of cell types and is known to cause hepatotoxicity and, in rare cases, death. 2) GM-CSF itself can induce systemic capillary leak syndrome, a condition in which intermittent leakage of intravascular fluids into the extravascular space can lead to low blood pressure and, in extreme cases, organ failure and shock. Therefore, ADV distribution and persistence was evaluated in samples from the wound bed and in selected tissues such as liver, kidney, and gonads. ADV was measured by two methods: 1) qualitative GFP fluorescence in tissue sections, in some cases with double labeling immunohistochemistry with antibody against ADV (Access Biomedical); and 2) quantitative RT-PCR of tissue homogenates with primers for the ADV vector.

For RT-PCR analysis, a pair of ADV vector-specific primers was used, and, as an internal control, a pair of primers specifying a 404 BP sequence from the murine acid ceramidase (MAC) gene. The sensitivity of this PCR assay in the laboratory was previously determined by analyzing a 10-fold serial dilution of purified vector DNA over the range of $1 \times 10^6$ copies to 100 copies per reaction and spiking in 2 µg of mouse DNA purified from control mouse ovary tissue. The sensitivity of this assay is less than 100 copies of ADV/GM-CSF per reaction (less than 100 copies/µg mouse DNA). This analysis permits assessment and monitoring of GM-CSF levels. At the time of sacrifice, each animal underwent a brief gross necropsy and selected organs were examined, removed, weighed and fixed for histopathology examination. These organs included liver and kidney.

Mechanisms of GM-CSF-Induced Wound Healing.

Skin samples from the wound sites were stained selectively to measure the effects of ADV/GM-CSF on mechanisms of wound healing, including:

a. Monocyte/macrophage recruitment, by immunostaining histological sections for monocytes and macrophages b. Recruitment of epithelial precursor cells by staining with antibody against the marker GATA2 (Keswani 2004)

c. Inflammation, e.g., measure the local inflammatory response induced by GM-CSF by comparing inflammatory markers in wounds treated with ADV with or without GM-CSF.

Biomechanical properties were also analyzed. Skin mechanical properties reflect the inherent structural and functional characteristics of the skin and provide additional information about the progression of wound healing that complement measures of contraction and histology. Mechanical properties included tensile stiffness N/mm) (a measure of the amount of force required to deform the skin, or extensibility) and load to failure (Newtons) (a measure of the force required to break the sample). When converted to stress-strain equivalents, the normalized load-deformation data represent intrinsic mechanical properties of the cross-sectional specimen geometry independent of variability in the width and thickness of the individual skin samples. Whereas histology describes cellular mechanisms and tissue adaptation at the ultrastructural level, mechanical property data provide a clinically relevant, functional assessment of wound healing quality.

Biomechanical Testing.

Biomechanical testing was conducted with an Instron servohydraulic materials testing system (model 8872, Canton, Mass., USA). First, specimen thickness was measured by a custom-designed electrical resistance gauge. Then, skin samples were clamped between sandpaper-covered plates of the actuator with a consistent grip-to-grip gauge length of 15 mm. They were centered within the clamps with a custom-made alignment apparatus. Tensile loads were measured with a 2.5 Ib. (1 1 .1 N) load transducer (Transducer Techniques, Temecula, Calif., USA). A preload of 0.02N was maintained for 2 minutes to define the initial length needed for engineering strain computations. Precision calipers were used to measure the grip-to-grip distance (specimen length) and the specimen width along the length of the sample. Synchronized load-deformation data was acquired by an A/D system with LabView software (National Instruments, Inc., Austin, Tex., USA). When converted to stress-strain equivalents, the normalized load-deformation data provided intrinsic mechanical properties reflective of the cross-sectional specimen geometry, and therefore accounted for variability in the width and thickness of skin samples. The skin samples were stretched until they broke, and the force and overall strain exerted on the samples was measured with the instrument based on the grip-to-grip displacement values. Local strain was measured by video tracking of surface markers and post-processed with image analysis software.

From the measured force and strain for each sample, one can calculate parameters such as: force in Newtons (N), stiffness (N/mm), ultimate tensile strength (MPa); maximum tangent modulus (MPa); strain energy distribution$_{max\ stress}$ (MPa); and strain energy distribution$_{failure}$ (MPa). Analysis of variance was used to determine overall differences between the treatment groups at each time point and post doc analysis with Tukey's HSD was used to determine differences between individual treatments, with $p<0.05$ being considered statistically significant.

Results

Tables 1 and 2 demonstrate the results of the mechanical testing in the NOD and BKS.Cg-m+/+Lepr$^{db}$ mice.

TABLE 1

Mechanical Testing: type 1 diabetic NOD mice (see table)

| Group (Vol: 200 ml) | Test Day | Age (wks) | HbA1c (%) | Pre-wounding BW (g) | Morning Glucose (mg/dL) | Glucose (2 hr-post insulin) Day 0 | Glucose (5 hr-post insulin) Day 7 | Pre-testing BW (g) | Morning Glucose (mg/dL) | Stiffness (N/mm) | Load to Failure (N) |
|---|---|---|---|---|---|---|---|---|---|---|---|
| ADV/mGM-CSF $5 \times 10^8$ | 14 | 30 | 7.4 ± 2.2 | 26.7 ± 1.4 | 487 ± 156 | 157 ± 106 | 178 ± 155 | 28.1 ± 1.5 | 502 ± 156 | 1.70 ± 0.3 | 4.21 ± 0.9 |
| Recombinant mGM-CSF | 14 | 30 | 7.7 ± 2.1 | 26.3 ± 1.5 | 514 ± 124 | 196 ± 119 | 127 ± 91 | 28.4 ± 1.2 | 488 ± 189 | 1.71 ± 0.2 | 3.71 ± 0.8 |
| DL-312 $5 \times 10^8$ (Vehicle) | 14 | 30 | 7.6 ± 2.1 | 26.4 ± 1.3 | 502 ± 170 | 228 ± 121 | 164 ± 142 | 27.9 ± 1.5 | 526 ± 157 | 1.49 ± 0.3 | 3.62 ± 0.8 |
| Saline (Negative Control) | 14 | 30 | 7.5 ± 2.2 | 26.4 ± 1.5 | 469 ± 168 | 209 ± 114 | 125 ± 101 | 27.5 ± 2.7 | 498 ± 157 | 1.50 ± 0.3 | 3.26 ± 1.0 |

TABLE 2

Mechanical Testing: type 1 diabetic NOD mice (see table)

| Group (Vol: 200 ul) | Testing Day | Age (wks) | Pre-wounding BW (g) | Glucose (mg/dL) | Pre-testing BW (g) | Glucose (mg/dL) | Stiffness (N/mm) | Load to Failure (N) |
|---|---|---|---|---|---|---|---|---|
| ADV/GM-CSF $5 \times 10^{10}$ | 10 | 9 | 31.8 ± 0.9 | 341 ± 133 | 33.9 ± 1.6 | 482 ± 50 | 0.29 ± 0.1 | 0.56 ± 0.2 |
| ADV/GM-CSF $5 \times 10^{8}$ | 10 | 9 | 31.2 ± 3.6 | 426 ± 161 | 30.9 ± 3.1 | 499 ± 52 | 0.50 ± 0.1 | 0.99 ± 0.3 |
| DL-312 $5 \times 10^{8}$ (Positive Controls) | 10 | 9 | 31.5 ± 3 | 404 ± 127 | 33.2 ± 3.5 | 493 ± 70 | 0.32 ± 0.2 | 0.54 ± 0.3 |
| Saline (Negative Controls) | 10 | 9 | 30.6 ± 4.1 | 429 ± 123 | 34.1 ± 4.7 | 550 ± 66 | 0.42 ± 0.1 | 0.78 ± 0.2 |
| ADV/GM-CSF $5 \times 10^{10}$ | 21 | 11 | 30.4 ± 2.8 | 394 ± 116 | 33.8 ± 3.2 | 588 ± 19 | 1.49 ± 0.3 | 3.71 ± 0.7 |
| ADV/GM-CSF $5 \times 10^{8}$ | 21 | 11 | 30 ± 2.4 | 394 ± 135 | 31.8 ± 5.7 | 553 ± 70 | 1.27 ± 0.2 | 4.18 ± 1.0 |
| DL-312 $5 \times 10^{8}$ (Positive Controls) | 21 | 11 | 31.1 ± 2.3 | 413 ± 61 | 33.2 ± 1.6 | 588 ± 24 | 1.13 ± 0.2 | 3.72 ± 0.6 |
| Saline (Negative Controls) | 21 | 11 | 31.2 ± 1.9 | 372 ± 88 | 34.2 ± 4.3 | 558 ± 67 | 1.17 ± 0.15 | 3.57 ± 0.6 |

FIGS. 1A-1D measure mechanical properties, specifically Stiffness (N/mm) (FIGS. 1A, 1C, respectively) and Load to Failure (N) (FIGS. 1B and 1D, respectively) for NOD Mice at 14 days (FIGS. 1A and 1B) and BKS.Cg-m+/+Lepr$^{db}$ mice at 10 days (FIGS. 1C and 1D), treated as described in the examples.

These results demonstrated that the ADV vector restores the skin integrity of diabetic wounds. Delivery of GM-CSF to incisional wounds of NOD mice resulted in increased load to failure (N) or load to failure compared to saline control at day 14 post wounding (p=0.03). The recombinant form of GM-CSF also showed no increase in mechanical properties compared to any of the control groups.

biomechanical testing also differs between the two: days 10 and 21 in the type 2 diabetic mice and at day 14 in the type 1 diabetic mice.

No mortality was found post wounding and intradermal injections in type 2 diabetic mice. Two NOD mice died at 7 days post wounding, and another at 12 days post wounding. All 3 mice were from the ADV/GM-CSF treated group.

Histological analysis revealed that treatment with GM-CSF $5 \times 10^{8}$ vp/wound at day 10 in BKS.Cg-m+/+mice, and at day 14 in NOD/LtJ mice versus controls has increased macrophage count. Analysis with H&E stain revealed increased number of cells in ADV/GM-CSF $5 \times 10^{8}$ vp treated wounds versus control wounds (p=0.042 and p=0.0051) in BKS.Cg-m+/+mice. These results are summarized in Tables 3 and 4.

TABLE 3

| Treatment | N= | H&E Epithelialization | # of cells/ HPF | Inflammation: acute or chronic | Mason Trichrome Granulation Tissue | Collagen | MOMA-2 # of Macrophages/ HPF |
|---|---|---|---|---|---|---|---|
| Treated (ADV/mGM-CSF $5 \times 10^{8}$ vp/wound) | 4 | 1.0 ± 0 | 314 ± 58 | 0.5 ± 0.6 | 0.26 ± 0.22 | 0.74 ± 0.22 | 14.3 ± 9.0 |
| Treated (rn GM-CSF 10 μg/wound) | 4 | 1.0 ± 0 | 287 ± 37 | 0.0 ± 0 | 0.06 ± 0.05 | 0.94 ± 0.05 | 6.8 ± 5.5 |
| Non-Treated DL-312 $5 \times 10^{8}$ vp/wound (Virus Vehicle only) | 4 | 1.0 ± 0 | 290 ± 48 | 1.0 ± 0.8 | 0.29 ± 0.25 | 0.71 ± 0.25 | 2.8 ± 4.3 |
| Non-Treated (Saline only) | 4 | 1.0 ± 0 | 259 ± 22 | 0.0 ± 0 | 0.15 ± 0.08 | 0.85 ± 0.08 | 9.8 ± 12.6 |

TABLE 4

| Treatment | N= | H&E Epithelialization | # of cells/ HPF | Inflammation: acute or chronic | Mason Trichrome Granulation Tissue | Collagen | CD-68 # of Macrophages/ HPF |
|---|---|---|---|---|---|---|---|
| Treated (ADV/mGM-CSF $5 \times 10^{8}$ vp/wound) | 9 | 1.0 ± 0 | 473 ± 88 | 0.25 ± 0.4 | 0.69 ± 0.20 | 0.33 ± 0.18 | 8.4 ± 9.2 |
| Non-Treated DL-312 $5 \times 10^{8}$ vp/wound (Virus Vehicle only) | 7 | 1.0 ± 0 | 283 ± 104 | 1.4 ± 0.75 | 0.77 ± 0.19 | 0.23 ± 0.19 | 0.8 ± 1.6 |
| Non-Treated (Saline only) | 8 | 1.0 ± 0 | 335 ± 57 | 1.0 ± 0.8 | 0.65 ± 0.13 | 0.35 ± 0.13 | 3.6 ± 5.6 |

The efficacy of ADV/GM-CSF is very distinct between the 2 different strains and type of mice used: type 1 versus type 2 diabetic mice. The optimal dose of the viral particles (vp) to be administered in unknown. The tissue collection for the The data demonstrates that intradermal administration of ADV/GM-CSF enhances tensile property, by increasing collagen deposition and by stimulating the migration of keratinocytes to wound sites in diabetic mice.

Granulocyte macrophage colony stimulating factor (GM-CSF) has a biological effect of recruiting and stimulating macrophages, critical cells in the wound that improves local immunity and secretes multiple growth factors and may reverse the etiologies characteristic of impaired healing due to diabetes. In this study, local sustained release of GM-CSF using adenovirus vehicle was studied to determine if reversal of the wound healing impairment in type 1 and type 2 diabetic mouse models could be achieved by 1) measuring skin biomechanical properties: load to failure (Newtons), the amount of force required to rupture the skin, and stiffness (Newtons/min), the amount of force required to deform the skin or resilience; 2) qualitative analysis of collagen deposition and epithelialization at the wound site via histological studies; 3) comparing migration rates of keratinocytes to the wound area via wound scratch assays.

The results demonstrate that GM-CSF stimulated healing (i.e. epithelialization) independent of recruiting macrophages. To achieve the local therapeutic effect of accelerated healing, sustained release and/or other appropriate selection of carrier and amount of the GM-CSF is necessary, as demonstrated by gene transfer using adenovirus vector expressing GM-CSF as a paradigm of local sustained delivery of GM-CSF.

Example 3

Effect of Human GM-CSF on Human Keratinocytes

Materials and Methods
Construction of the Virus Vector:
The human cDNA for GM-CSF was cloned into a recombinant adenovirus vector. Human umbilical vein endothelial cells (HUVEC) were harvested from fresh umbilical cords, grown until confluency of a 100 mm plate and homogenized for the total RNA extraction. Total RNA was extracted with the RNeasy™ kit from Qiagen Inc. First strand cDNA was amplified from the RNA by RT-PCR with oligo-dT primers using the Superscript™ I1 RT PCR kit from Life Technologies. The product corresponding to the size of GM-CSF was gel-purified and cloned into pBluescript (Stratagene), using the HindIII and XbaI restriction sites.

The vector, as constructed, resulted in gene transfer, ascertained by transgene expression in target cells in culture. JC cells, a GM-CSF-negative murine breast cancer cell line which is easily transducible by adenovirus, were infected with virus of different plaques of ADV/hGM-CSF or ADV.beta Gal (beta-galactosidase, negative control) with an MOI of 100. GM-CSF was measured after 48 hours in the conditioned supernatant by hGM-CSF ELISA, (R&D Systems), according to the manufacturer's instructions. The ELISA results for hGMCSF of conditioned supernatant of JC cells transduced are: (1) virus of different plaques of ADV/hGMCSF: pl. 11-1; 11-2; 11-3; 11-9; 13-1; 16-1; (2) control vector (beta-Gal); and supernatant of uninfected JC cells. GMCSF standard curve with recombinant GMCSF protein was supplied by the manufacturer (InvivoGen, San Diego, Calif.).

Results
GM-CSF accelerates migration and increases proliferation of human keratinocytes in vitro assay of wound healing epithelialization. GM-CSF increases keratinocytes migration in vitro. Cells were treated with mitomycin C (10 µg/ml) for one hour to eliminate proliferation. Cells were placed in basal medium (with no growth factors or hormones) and photographed immediately after the scratch. All scratches were photographed at the 0 time point and re-photographed in the same field 24 hrs and 48 hrs later. When normal human keratinocytes grown in a tissue culture dish are "wounded" by a scratch, the cells migrate over the scratch to close the gap. This approach was utilized to test how GM-CSF affects keratinocyte migration and proliferation. Keratinocytes were incubated in the presence and absence of recombinant GM-CSF and observed keratinocyte migration during a period of 48 hrs. EGF was used as a positive control because it is an established potent stimulator of both migration and proliferation of keratinocytes.

The results showed that GM-CSF strongly accelerated cell migration after 24, and more significantly, after 48 hrs the cells were actively migrating. The keratinocytes incubated in the presence of GM-CSF migrated significantly faster after 48 hrs and almost closed the gap. Similarly, cells incubated with EGF also migrated significantly faster than untreated, control cells. In order to distinguish if GM-CSF affects migration directly or indirectly, by promoting proliferation, an analogous experiment with mitomycin C-treated keratinocytes was performed, with similar results. GM-CSF strongly accelerated migration of mitomycin C-treated keratinocytes, thus confirming that GM-CSF has direct effect on keratinocyte migration.

These findings are very important not only clinically but also in cosmetic applications because they establish that GM-CSF promotes keratinocyte migration which can induce smooth appearance of the epidermis. For example, in dermabrasion (removal or scrubbing off the epidermal layer) or any method of exfoliation, GM-CSF would stimulate keratinocytes to cover the damages areas.

Example 4

GM-CSF Stimulates Migration of Activated Keratinocytes and Fibroblasts from Patients with Chronic Wounds To test the effects of GM-CSF on epithelialization, which is very important in cosmetology especially for laser resurfacing, recombinant GMCSF was tested using an in vitro scratch model to measure keratinocyte migration.

Materials and Methods
Primary human keratinocytes were grown in low calcium to emulate the wound healing phenotype and in high calcium to emulate the differentiated phenotype. Patient biopsies of venous ulcers from three wound locations: the healing edge, the non-healing edge and the wound base were obtained and primary fibroblasts were derived from them. The migration capacity of cells was tested in the presence and absence of GM-CSF. Surface area was measured at time 0, 24 hours and 48 hours after wounding. Cells were observed over a period of time, up to 10 days.

Figure 3A:
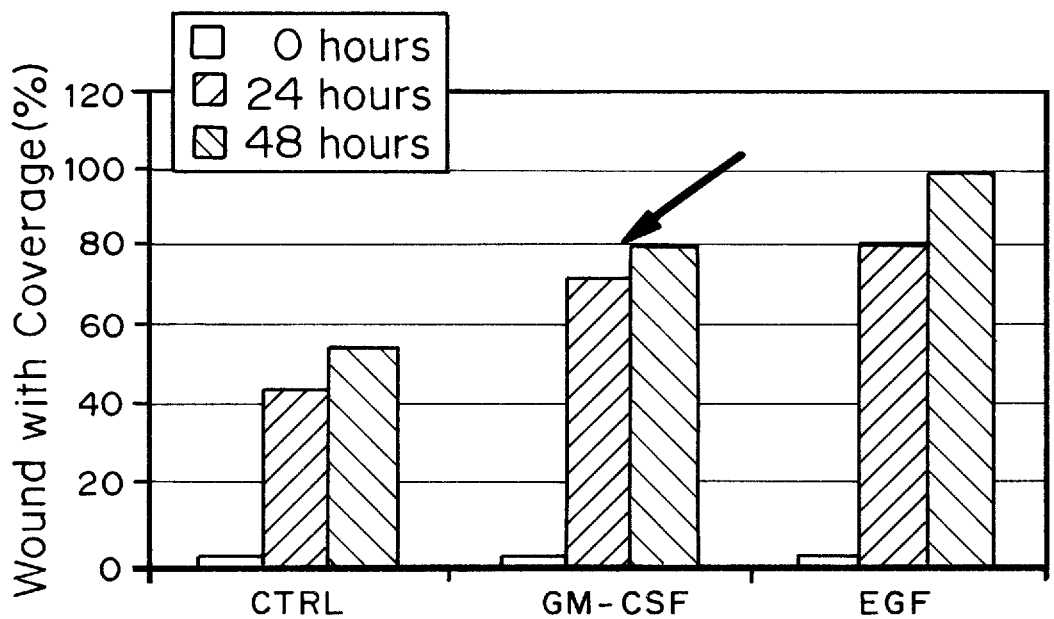
FIGS. 3A and 3B show the results of recombinant GMCSF tested using, an in vitro scratch model to measure keratinocyte migration at 0, 24 and 48 hours in calcium treated (FIG. 3A or untreated (FIG. 3B) keratinocytes.
Figure 3B:
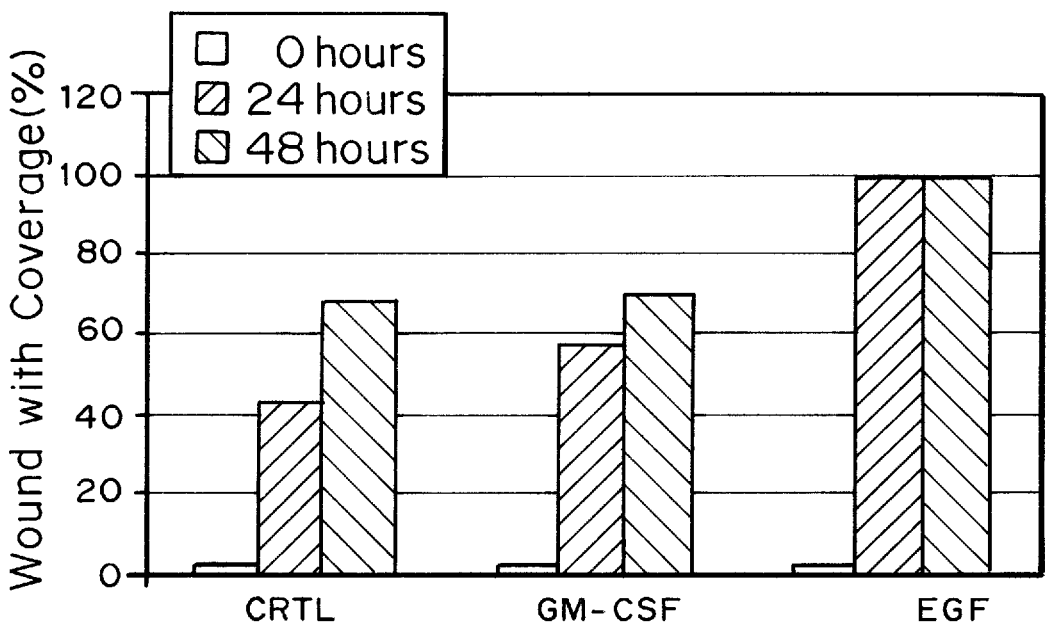

Results
Keratinocytes grown in culture medium containing low calcium resemble the activated keratinocytes, the cells that actively participate in tissue repair and regeneration. However, keratinocytes grown in a high calcium medium change their phenotype and become differentiated. As their proliferation rate decreases, they form desmosomal junctions and start stratifying in culture. Once committed to differentiation they progressively lose the regenerative potential, i.e. differentiating cells stop dividing. Interestingly, when GM-CSF was tested using differentiated keratinocytes (i.e. those grown in high calcium conditions) it was found that GM-CSF did not stimulate migration or proliferation in scratch assay experiments (FIG. 3b). These clinically relevant findings establish that GM-CSF promotes epithelialization and specifically targets those keratinocytes that have capacity for regeneration. In addition to contributing the smooth appearance of the skin it may also be used for rapid resurfacing after laser treatments, dermabrasion or exfoliation.

GM-CSF strongly accelerated cell migration after 24, and more significantly, after 48 hrs, the cells were actively migrating. The keratinocytes incubated in the presence of GM-CSF migrated significantly faster compared to untreated controls. Cell migration was measured and quantified by three blinded investigators. Graphs are presented in the FIG. 3A. Similarly, cells incubated with EGF also migrated significantly faster than untreated, control cells. In order to distinguish if GM-CSF affects migration directly or indirectly, by promoting proliferation, we completed analogous experiment only with mitomycin C-treated keratinocytes and found similar results. GMCSF strongly accelerated migration of mitomycin C-treated keratinocytes, thus confirming that GM-CSF has direct effect on keratinocyte migration.

In order to distinguish if GM-CSF affects migration directly or indirectly, by promoting proliferation; analogous experiments were conducted only with mitomycin C-treated keratinocytes and similar results were obtained. GMCSF strongly accelerated migration of mitomycin C-treated keratinocytes, thus confirming that GM-CSF has direct effect on keratinocyte migration.

The GMCSF effects on keratinocytes and fibroblasts (both human and mouse) that were observed were determined either within first 24 hrs (human cells) or 10 days, suggesting a rapid biological response. Most clinical studies using retinoids have reported noticeable benefits only after six months of treatment, and within two weeks for Botox acts. Thus GM-CSF action is not only broader as it encompass beneficial cosmetic effects of both retinoids and botox, but it also has very fast effect.

Removing differentiated keratinocytes from the wound should enhance epithelization when treated with GM-CSF. GM-CSF differentially stimulates fibroblast migration depending on where in the wound they came from. These findings show that growth factor therapy will be effective in promoting epithelization when applied to the edges of a wound and not the wound bed.

Example 5

Dermal Effects of GM-CSF (a) GM-CSF Promotes Collagen Deposition and its Proper Alignment.

One of the hallmarks of wrinkles is incorrect deposition of collagen and imperfect skin cell layering. Sirius red staining with polarized light microscopy on three treatment groups was used to test if GM-CSF affects collagen deposition and its alignment.

Saline treated control wounds showed minimal birefringence from collagen fibers which appeared as greenish yellow birefringence. These collagen fibers were short, thin and arranged in a random pattern. The greenish-yellow birefringence of these collagen fibers is typical of young immature granulation tissue. There was minimal red birefringence on the surface of the granulation tissue from the keratin laid-down by keratinocytes within the epidermal cell layer. In the saline treated mice there is little collagen deposited and that newly deposited collagen is poorly organized. Empty viral particles treated wounds showed a slight increase in the greenish-yellow birefringence intensity, with collagen fibers arranged in a more parallel fashion compared to saline treated controls. The Sirius red stained polarized light viewed ADV/GM-CSF treated wounds showed an intense reddish-yellow birefringence pattern, with collagen fibers that were long, thick and had a strong association with one another. The intense reddish-yellow color was in contrast to the greenish-yellow birefringence color of the saline and empty viral particle treated wounds. The reddish-yellow intense birefringence was consistent with a greater amount of collagen deposited, which was laid down in a more organized fashion. This pattern of birefringence suggested better organization of the newly deposited granulation tissue in these treated wounds.

In summary, it was determined that not only does GM-CSF induce collagen deposition but it also promotes its proper alignment. More collagen in the skin means a thicker dermis, and thicker skin protects the skin from UV and also reverses existing damage. More collagen production in the skin will lead to stronger skin which may prevent formation of wrinkles that are generated from grimacing and decrease the appearance of existing ones generated in the process of aging. Also, not only is there more collagen with GM-CSF treatment, there is good orientation of the collagen, which makes the collagen more stable and less susceptible to degradation. Most factors that lead to aging such as free radicals induce matrix metalloproteinases (MMPs), which degrade collage. When not properly aligned, collagen is easier to degrade. Therefore, GM-CSF will reduce aging and UV-mediated collagen degradation.

(b) GM-CSF Increases Dermal Thickness.

Histological analyses of wounds treated with saline, empty ADV vector and ADV/GM-CSF show significant increase in granulation tissue in GM-CSF treated wounds when compared to either of the controls (saline or empty vector). This indicates that GM-CSF stimulates collagen deposition and stimulates fibroblast proliferation, thus acting as dermal filler. Fibroblasts make collagen, thus, not only does GM-CSF directly stimulate fibroblast proliferation (which equals more fibroblasts), GM-CSF also induces increases collagen deposition by these fibroblasts. More fibroblast equals more collagen. Thinning of the skin is one of the signs of aging that leads to wrinkling and sagging. Therefore, GM-CSF effects on fibroblast proliferation should reverse this effect.

(c) GM-CSF Increases Tensile Strength, i.e. Makes Skin Strong

It was postulated that if GM-CSF increases the mechanical properties of skin (tensile and breaking strength), it will increase the strength of the skin, thus prevent wrinkles and reduce their appearance. Sustained delivery of GM-CSF using ADV/GM-CSF and a diabetic mouse model was used to test if GM-CSF affects tensile and breaking strength of skin, Linear Incisional wounds were created on the dorsum of 57 female BKS.Cg-m+/+Lepr$^{db}$ type 2 diabetic mice. Prior to wounding, the animals were acclimatized for 2 weeks by being placed in individual cages. They were shaved at least one day prior to wounding, and then anesthetized with a mixture of ketamine and xylazine prior to wounding. A 30-mm linear incision was initiated 5 mm below the last cervical vertebra on the dorsum of each animal in a longitudinal direction, Intradermal injections were administered at both sides of the incision at the 3rd suture location only.

Update Results

Example 6

GMCSF Increase Cellularity and Induces Cell Infiltration of Other Cell Types

Materials and Methods

Histology specimens were collected from wounds treated with saline, empty vector or ADV/GM-CSF and immunohistochemistry was performed to stain for macrophages. Cells stained positive for CD-68 were counted from 30 randomized samples for each condition by 3 independent investigators blinded for the treatment.

Results

Histological analysis revealed that treatment of BKS.Cg-m+/+Lepr$^{db}$ mice with GM-CSF 5×10$^8$ vp/wound on day 10 after wounding increased macrophage count as compared to controls as shown in Table 5 below. This was also observed on day 14 in the comparison of treated NOD/LtJ mice versus controls. Effects are more pronounced in db/db mice (more than two fold) whereas in NOD there is similar tendency of increase of 45%. Moreover, analysis with H&E stain revealed increased number of cells in ADV/GM-CSF 5×10$^8$ vp treated wounds versus control wounds (p=0.042 and p=0.0051) in BKS.Cg-m+/+Lepr$^{db}$ mice. Infiltrate of specific cell types, such as macrophages, is an indication that by attracting specific cells into the site of application GM-CSF acts as individual cell therapy. Furthermore, macrophages provide factors that can also revive (stimulate) fibroblasts and keratinocytes to become more active.

TABLE 5

Effect of GM-CSF on infiltration of specific cell types in NOD (macrophages) and db/db mice (CD-68 cells).

| | NOD MICE (at day 14) | db/db MICE (at day 10) | |
| --- | --- | --- | --- |
| Treatment | # of Macrophages/ HPF | Treatment (Number of animals, N) | # of Macrophages/ HPF |
| ADV/mGM-CSF 5 × 10$^8$ vp/wound | 14.3 ± 9.0 | ADV/mGM-CSF 5 × 10$^8$ vp/wound (N = 9) | 8.4 ± 9.2 |
| rmGM-CSF 10 μg/wound) | 6.8 ± 5.5 | N/A | N/A |
| DL-312 5 × 10$^8$ vp/wound (Virus Vehicle only) | 2.8 ± 4.3 | DL-312 5 × 10$^8$ vp/wound (N = 7) (Virus Vehicle only) | 0.8 ± 1.6 |
| Saline | 9.8 ± 12.6 | Saline (N = 8) | 3.6 ± 5.6 |

Example 7

GM-CSF Stimulates Subdermal Adipose Tissue Fat Production 8 weeks old female BKS.Cg-m+/+Lepr$^{db}$ mice were anesthetized by intraperitoneal (IP) injection of a ketamine and xylazine mixture and shaved the day before experimentation. Full thickness wounds 1.4 cm diameter were made with a template (George Tieman Inc., NY) and the edges were tattooed. The marked area was excised with scissors to remove the epidermis, dermis, and panniculus carnosus. An 0.8 cm full-thickness circle of skin were removed from the middle of the back. Under current standards of wound care, ulcers in diabetic patients take between 56 and 90 days to heal (if indeed they do heal), but full thickness wounds in these diabetic mice heal within 34 days.

Full-thickness excisional wounds were produced in glucose-controlled BKS.Cg-m+/+Lepr$^{db}$ mice and treated with injections of ADV-mGM-CSF. ADV constructs or controls were injected intradermally up to a maximum volume of 400 pl at three sites around the wound perimeter, which is marked with indelible ink. The dose range was selected in half-log units to flank 1×10$^8$ PFUs. Treatment groups are illustrated in the tables. The wounds were dressed with a clear occlusive dressing and after recovery, the mice returned to their cages and observed daily to assess wound healing.

Mice were observed daily, and wound healing and adverse effects assessed quantitatively weekly for 3-8 weeks. Histological evaluation was performed with day 10 wounds of BKS.Cg-m+/+Lepr$^{db}$ mice to correlate wound biomechanical results. Freshly excised wounds, 30 mm×8 mm skin strip perpendicular to the third incision was obtained 10 days post wounding in BKS.Cgm+/+Lepr$^{db}$ mice and 14 days post wounding in NOD mice. The excised skin were fixed overnight in 4% parafomaldehyde, bisected and processed for paraffin embedding. Five-micron sections were cut and stained with (1) H&E staining, for evaluation of re-epithelialization, (2) Mason trichrome. Immunohistochemistry were performed on sections with MOMA-21anti-CD68 (macrophages). Investigators blinded to the treatment protocol will perform the assessments. Fixation with 4% paraformaldehyde requires specimen transfer into 70% ethanol after 24-hours of fixation. If this is not performed, antigen retrieval is necessary for any immunohistochemistry, or allow fixation in Zinc-Tris instead.

Sucutaneous fat provides the base for the dermis and with aging, the fat cells become smaller. This leads to more noticeable wrinkles and sagging, as the fat cells cannot "fill in" the damage from the other layers. The effects of GM-CSF on subcutaneous fat indicates that GM-CSF can promote "filler appearance" of the skin, which also prevents additional wrinkling, because if the dermis sits on a solid base, it makes the dermis stronger.

In summary, the examples demonstrate that GM-CSF has powerful anti-aging effects on skin. The results establish that GM-CSF induces collagen production and proper alignment, increases tissue strength, promotes epidermal migration and proliferation, increasing the smoothness of the skin. This means that if applied topically or locally injected it should have a profound anti-aging effect that will not only reduce the appearance of wrinkles but prevent their new formation simultaneously. In addition, it acts as an attractant to other cell types, such as macrophages, thus acting as an individual cell therapy agent. can also be administered to the skin following dermal abrasion, for treating conditions wherein collagen stimulation, epidermal stimulation or fat deposition would be beneficial, or for enhancing epidermal. Further application of GM-CSF include but are not limited to lip augmentation, wrinkle reduction, enhancement of facial fullness, fill deep creases, build up contours, dermal abrasion, reconstructive surgery, any condition where UV radiation is needed, treatment with skin grafts, radiation injury, tobacco injury to skin, and after chemotherapy or anticancer therapy.

We claim:

1. A cosmetic method of treating skin to enhance skin quality comprising administering topically or by intradermal or subcutaneous injection to wrinkled, saggy or thinned skin an effective amount of a composition to promote an effect selected from the group consisting of keratinocyte migration, fibroblast proliferation, macrophage infiltration, and collagen deposition, wherein the active ingredient consists of GM-CSF or nucleic acid molecules expressing GM-CSF.

2. The method of claim 1 comprising administering to the surface of the skin to be treated a composition consisting of GM-CSF or nucleic acid molecules expressing GM-CSF in a formulation for topical application to the skin.

3. The method of claim 1 comprising administering by intradermal or subcutaneous injection at or near the skin to be treated a composition consisting of GM-CSF or nucleic acid molecules expressing GM-CSF in a pharmaceutically acceptable carrier for injection.

4. The method of claim 1 wherein the composition comprises a sustained or controlled release formulation providing GM-CSF at the site to be treated for between one and 10 days.

5. The method of claim 1 wherein an effective amount of GM-CSF is administered to increase keratinocyte migration to the treated skin.

6. The method of claim 1 further comprising removing or scrubbing off some or all of the epidermal layer of the skin to be treated prior to or at the time of administration of the GM-CSF.

7. The method of claim 1 wherein an effective amount of GM-CSF is administered to increase keratinocyte migration, fibroblast proliferation and infiltration of macrophages.

8. The method of claim 7 wherein an effective amount of GM-CSF is administered to promote fibroblast proliferation to the skin to be treated.

9. The method of claim 7 wherein the GM-CSF is administered in an amount effective to promote collagen deposition.

10. The method of claim 9 wherein the GM-CSF is administered in an amount effective to increase or align the collagen to decrease wrinkling or sagging of the skin.

11. The method of claim 10 wherein the collagen is oriented to increase stability of the dermis and decrease susceptibility to degradation.

12. The method of claim 1 wherein the GM-CSF is administered in an amount effective to stimulate infiltration of macrophages into the skin to be treated.

13. The method of claim 1 wherein the GM-CSF is administered in an amount effective to increase sub-dermal fat.

14. The method of claim 1 wherein the GM-CSF is administered to the skin in combination with an exfolliant or laser treatment.

15. The method of claim 1, wherein at least about $1\times10^6$ recombinant viral particles are administered to the skin.

16. The method of claim 1, wherein the composition is administered to wrinkled skin.

17. A cosmetic method of treating wrinkled, saggy or thinned skin to enhance skin quality comprising a) removing or scrubbing off some or all of the epidermal layer of the skin, and b) administering topically or by intradermal or subcutaneous injection to the skin a composition comprising GM-CSF or nucleic acid molecules expressing GM-CSF in an effective amount to promote an effect selected from the group consisting of keratinocyte migration, fibroblast proliferation, macrophage infiltration, and collagen deposition.

18. The method of claim 17, wherein some or all of the epidermal layer of the skin is removed with an exfolliant or laser treatment.

19. The method of claim 1, wherein the composition is administered to skin thinned.

20. The method of claim 19, wherein the composition is administered to thinned wrinkled skin.

* * * * *

SEQUENCE LISTING

<160> NUMBER OF SEQ ID NOS: 3

<210> SEQ ID NO 1
<211> LENGTH: 144
<212> TYPE: PRT

```
<213> ORGANISM: Homo sapiens

<400> SEQUENCE: 1

Met Trp Leu Gln Ser Leu Leu Leu Gly Thr Val Ala Cys Ser Ile
1               5                   10                  15

Ser Ala Pro Ala Arg Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 2
<211> LENGTH: 780
<212> TYPE: DNA
<213> ORGANISM: Homo sapiens

<400> SEQUENCE: 2
acacagagag aaaggctaaa gttctctgga ggatgtggct gcagagcctg ctgctcttgg      60
gcactgtggc ctgcagcatc tctgcacccg cccgctcgcc cagccccagc acgcagccct     120
gggagcatgt gaatgccatc caggaggccc ggcgtctcct gaacctgagt agagacactg     180
ctgctgagat gaatgaaaca gtagaagtca tctcagaaat gtttgacctc caggagccga     240
cctgcctaca gacccgcctg gagctgtaca agcagggcc gcggggcagc ctcaccaagc     300
tcaagggccc cttgaccatg atggccagcc actacaagca gcactgccct ccaaccccgg     360
aaacttcctg tgcaacccag attatcacct ttgaaagttt caagagaaac ctgaaggact     420
ttctgcttgt catccccttt gactgctggg agccagtcca ggagtgagac cggccagatg     480
aggctggcca gccggggag ctgctctctc atgaaacaag agctagaaac tcaggatggt     540
catcttggag ggaccaaggg gtgggccaca gccatggtgg gagtggcctg gacctgccct     600
gggccacact gaccctgata caggcatggc agaagaatgg gaatatttta tactgacaga     660
aatcagtaat atttatatat ttatatttt aaaatattta tttatttatt tatttaagtt     720
catattccat atttattcaa gatgttttac cgtaataatt attattaaaa atatgcttct     780

<210> SEQ ID NO 3
<211> LENGTH: 141
<212> TYPE: PRT
<213> ORGANISM: Mus musculus

<400> SEQUENCE: 3

Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
```

-continued

```
        35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Gly Gln Lys
    130                 135                 140
```